(12) United States Patent
Nguyen et al.

(10) Patent No.: US 10,502,730 B2
(45) Date of Patent: Dec. 10, 2019

(54) AUTOMATED IMAGING AND ANALYSIS OF THE HEMAGGLUTINATION INHIBITION ASSAY (HAI)

(71) Applicant: Sanofi Pasteur VaxDesign Corporation, Orlando, FL (US)

(72) Inventors: Michael Nguyen, Oviedo, FL (US); Robert Parkhill, Oviedo, FL (US)

(73) Assignee: SANOFI PASTEUR VAXDESIGN CORPORATION, Orlando, FL (US)

(*) Notice: Subject to any disclaimer, the term of this patent is extended or adjusted under 35 U.S.C. 154(b) by 0 days.

(21) Appl. No.: 16/002,305

(22) Filed: Jun. 7, 2018

(65) Prior Publication Data

US 2018/0292397 A1 Oct. 11, 2018

Related U.S. Application Data

(62) Division of application No. 14/811,615, filed on Jul. 28, 2015, now Pat. No. 10,012,643.

(60) Provisional application No. 62/029,922, filed on Jul. 28, 2014.

(51) Int. Cl.
| | | |
|---|---|---|
| *B01L 3/00* | (2006.01) | |
| *G01N 33/543* | (2006.01) | |
| *G01N 35/02* | (2006.01) | |
| *B01L 9/00* | (2006.01) | |
| *G01N 33/53* | (2006.01) | |

(52) U.S. Cl.
CPC ............ *G01N 33/543* (2013.01); *B01L 9/52* (2013.01); *B01L 9/523* (2013.01); *G01N 33/5304* (2013.01); *G01N 35/025* (2013.01); *G01N 35/028* (2013.01); *G01N 2333/11* (2013.01); *G01N 2469/10* (2013.01)

(58) Field of Classification Search
None
See application file for complete search history.

(56) References Cited

U.S. PATENT DOCUMENTS

| 6,121,054 A | 9/2000 | Lebl |
|---|---|---|
| 2001/0002985 A1 | 6/2001 | Kleinsasser |
| 2001/0038809 A1 | 11/2001 | Burbaum |
| 2006/0238765 A1 | 10/2006 | Shah |
| 2007/0110638 A1 | 5/2007 | Heiner |

(Continued)

FOREIGN PATENT DOCUMENTS

| DE | 40 13 588 | 11/1991 |
|---|---|---|
| WO | 2014/015194 | 1/2014 |

OTHER PUBLICATIONS

International Search Report and Written Opinion of the International Searching Authority, dated Oct. 30, 2015, in International application No. PCT/US15/42527.

(Continued)

*Primary Examiner* — Erik B Crawford
(74) *Attorney, Agent, or Firm* — Wenderoth, Lind & Ponack, L.L.P.

(57) ABSTRACT

A system and method provide for high through put determination of agglutination states. The system includes a rotating table and multiple plate tilting stations. The system also includes one or more optical paths positioned to image entire plate arrays in tilted and/or untilted configurations. The system preferably includes image analysis software to analyze an image of an array of test wells and determine an agglutination state of each well based on the image analysis.

20 Claims, 33 Drawing Sheets
(17 of 33 Drawing Sheet(s) Filed in Color)

(56) References Cited

U.S. PATENT DOCUMENTS

| | | |
|---|---|---|
| 2009/0213382 A1 | 8/2009 | Tracy et al. |
| 2011/0097705 A1 | 4/2011 | Kachurin et al. |
| 2012/0202225 A1 | 8/2012 | Knutson |
| 2012/0309103 A1 | 12/2012 | Gambini |
| 2012/0309636 A1 | 12/2012 | Gibbons et al. |
| 2014/0045170 A1 | 2/2014 | Patel et al. |
| 2014/0073043 A1 | 3/2014 | Holmes |

OTHER PUBLICATIONS

Extended European Search Report dated Dec. 12, 2017 in European Application No. 15826988.6.

Nguyen et al., "Automated Imaging and Analysis of the Hemagglutination Inhibition Assay", Journal of Laboratory Automation, 21(2):287-296 (2016).

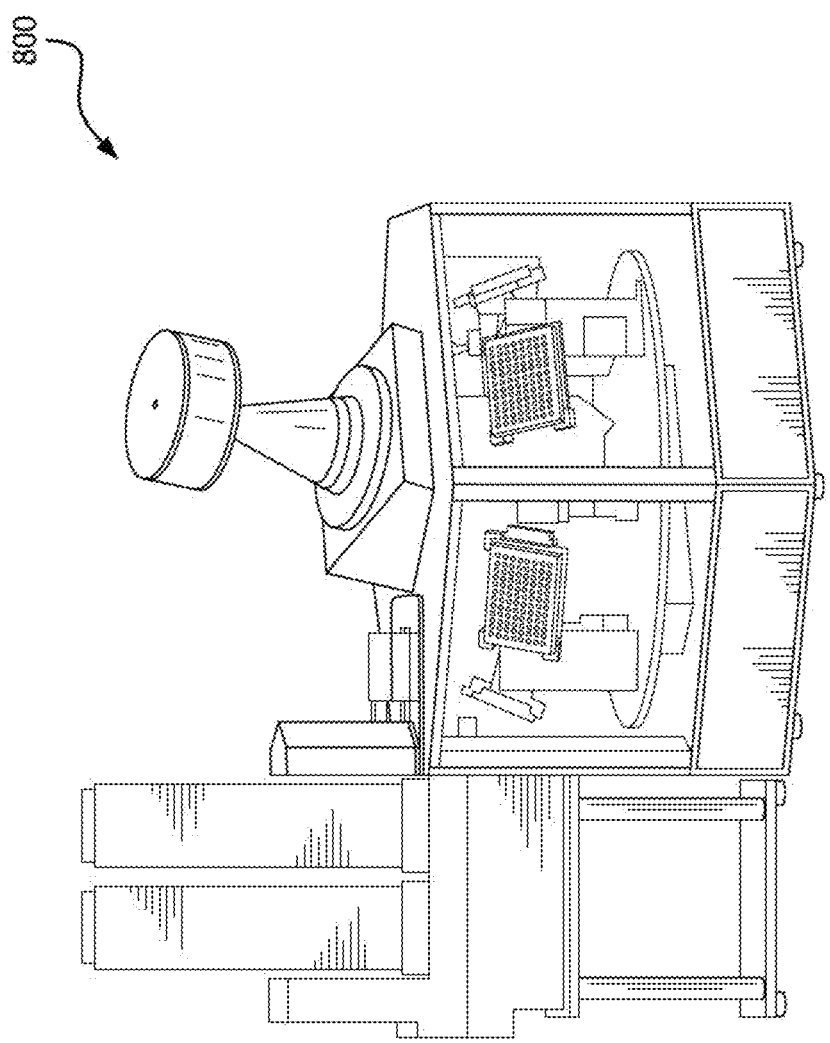

| Flu Antigen | Bleed | N | Slope (95%CI) | % Agreement | GMT (1/Dil) Manual | GMT (1/Dil) Auto | Percent Difference | GMTR (auto/manual) (95%CI) | Serostatus at 1:40 |
|---|---|---|---|---|---|---|---|---|---|
| A/California /07/2009 [H1N1] | All | 60 | 1.01 (0.96,1.05) | 100 (60/60) | 182.78 | 152.83 | -16.38% | 0.836 (0.798,0.876) | 100% (60/60) |
|  | Pre | 30 | 0.98 (0.92,1.05) | 100 (30/30) | 110.65 | 94.07 | -14.98% | 0.850 (0.792,0.913) | 100% (30/30) |
|  | Post | 30 | 1.08 (1.01,1.17) | 100 (30/30) | 301.93 | 248.28 | -17.77% | 0.822 (0.773,0.875) | 100% (30/30) |
| A/Victoria /361/2011 [H3N2] | All | 60 | 0.99 (0.95,1.03) | 100 (60/60) | 157.17 | 140.08 | -10.88% | 0.891 (0.850,0.935) | 98% (59/60) |
|  | Pre | 30 | 0.98 (0.93,1.03) | 100 (30/30) | 93.97 | 82.81 | -11.88% | 0.881 (0.823,0.944) | 97% (29/30) |
|  | Post | 30 | 0.99 (0.93,1.06) | 100 (30/30) | 262.90 | 236.96 | -9.86% | 0.901 (0.844,0.963) | 100% (30/30) |
| B/Brisbane /60/2008 | All | 60 | 1.01 (0.98,1.05) | 100 (60/60) | 56.17 | 56.20 | 0.06% | 1.001 (0.965,1.037) | 100% (60/60) |
|  | Pre | 30 | 1.01 (0.96,1.06) | 100 (30/30) | 47.53 | 47.55 | 0.04% | 1.000 (0.945,1.059) | 100% (30/30) |
|  | Post | 30 | 1.01 (0.96,1.07) | 100 (30/30) | 66.37 | 66.43 | 0.08% | 1.001 (0.956,1.048) | 100% (30/30) |
| B/Brisbane /60/2008 Ether | All | 60 | 0.98 (0.95,1.01) | 100 (60/60) | 298.43 | 298.40 | -0.01% | 1.000 (0.964,1.037) | 100% (60/60) |
|  | Pre | 30 | 0.99 (0.95,1.02) | 100 (30/30) | 250.89 | 250.85 | -0.02% | 1.000 (0.955,1.047) | 100% (30/30) |
|  | Post | 30 | 0.97 (0.92,1.03) | 100 (30/30) | 354.98 | 354.96 | -0.01% | 1.000 (0.945,1.058) | 100% (30/30) |

FIG. 28

| Flu Strains | Bleed | N | Seroprotection (1:40) | | Seroconversion | | GMTR (Post/Pre) | |
|---|---|---|---|---|---|---|---|---|
| | | | Manual | Auto | Manual | Auto | Manual | Auto |
| A/California /07/2009 [H1N1] | All | 60 | N/A | N/A | | | | |
| | Pre | 30 | 93%(28/30) | 93%(28/30) | 27% (8/30) | 27% (8/30) | 2.73 | 2.64 |
| | Post | 30 | 100%(30/30) | 100%(30/30) | | | | |
| A/Victoria/ 361/2011 [H3N2] | All | 60 | N/A | N/A | | | | |
| | Pre | 30 | 83%(25/30) | 87%(26/30) | 40% (12/30) | 37% (11/30) | 2.80 | 2.86 |
| | Post | 30 | 100%(30/30) | 100%(30/30) | | | | |
| B/Brisbane /60/2008 | All | 60 | N/A | N/A | | | | |
| | Pre | 30 | 70%(21/30) | 70%(21/30) | 10% (3/30) | 7% (2/30) | 1.40 | 1.40 |
| | Post | 30 | 73%(22/30) | 73%(22/30) | | | | |
| B/Brisbane /60/2008 Ether | All | 60 | N/A | N/A | | | | |
| | Pre | 30 | 90%(27/30) | 90%(27/30) | 10% (3/30) | 17% (5/30) | 1.41 | 1.42 |
| | Post | 30 | 97%(29/30) | 97%(29/30) | | | | |

FIG. 29

| Flu Antigen | Bleed | N | Slope (95%CI) | % Agreement | Percent Difference | Serostatus at 1:40 |
|---|---|---|---|---|---|---|
| A/California /07/2009 [H1N1] | All | 60 | 1.01 (0.99,1.02) | 100 (60/60) | -2.9% | 100% (60/60) |
| A/Victoria/ 361/2011 [H3N2] | All | 60 | 1.02 (1.00,1.04) | 100 (60/60) | -3.4% | 98% (59/60) |
| A/Victoria/ 210/2009 [H3N2] | All | 60 | 1.00 (1.00,1.00) | 100 (60/60) | -0.6% | 100% (60/60) |
| A/Brisbane /59/2007 [H1N1] | All | 54 | 1.00 (0.99,1.02) | 100 (54/54) | -1.9% | 100% (54/54) |
| A/New Caledonia/20/99 [H1N1] | All | 54 | 1.00 (0.99,1.02) | 100 (54/54) | +1.9% | 100% (54/54) |
| A/Texas/50/2012 [H3N2] | All | 60 | 1.00 (0.98,1.02) | 100 (60/60) | -3.4% | 100% (60/60) |
| B/Brisbane /60/2008 [Whole] | All | 60 | 0.99 (0.97,1.01) | 100 (60/60) | -2.8% | 100% (60/60) |
| B/Brisbane /60/2008 Ether | All | 60 | 1.01 (0.99,1.03) | 100 (60/60) | +1.8% | 98% (59/60) |
| B/Massachusetts /02/2012 [Whole] | All | 60 | 0.99 (0.97,1.01) | 100 (60/60) | -1.7% | 100% (60/60) |
| B/Massachusetts /02/2012 Ether | All | 60 | 1.01 (0.99,1.03) | 100 (60/60) | +2.9% | 100% (60/60) |

FIG. 30

| Flu Strains | Bleed | N | Seroprotection (1:40) | | Seroconversion | | GMTR (Post/Pre) | |
|---|---|---|---|---|---|---|---|---|
| | | | Manual | Auto | Manual | Auto | Manual | Auto |
| A/Texas/50/2012 [H3N2] | All | 60 | N/A | N/A | | | | |
| | Pre | 30 | 87%(26/30) | 87%(26/30) | 40%(12/30) | 40%(12/30) | 3.48 | 3.52 |
| | Post | 30 | 100%(30/30) | 100%(30/30) | | | | |
| A/California/07/2009 [H1N1] | All | 60 | N/A | N/A | | | | |
| | Pre | 30 | 93%(28/30) | 93%(28/30) | 27%(8/30) | 27%(8/30) | 2.86 | 2.83 |
| | Post | 30 | 100%(30/30) | 100%(30/30) | | | | |
| A/Victoria/361/2011 [H3N2] | All | 60 | N/A | N/A | | | | |
| | Pre | 30 | 80%(24/30) | 80%(24/30) | 40%(12/30) | 37%(11/30) | 3.29 | 3.21 |
| | Post | 30 | 100%(30/30) | 97%(29/30) | | | | |
| A/Victoria/210/2009 [H3N2] | All | 60 | N/A | N/A | | | | |
| | Pre | 30 | 87%(26/30) | 87%(26/30) | 37%(11/30) | 37%(11/30) | 3.32 | 3.29 |
| | Post | 30 | 100%(30/30) | 100%(30/30) | | | | |
| B/Massachusetts/02/2012 | All | 60 | N/A | N/A | | | | |
| | Pre | 30 | 63%(19/30) | 63%(19/30) | 17%(5/30) | 17%(5/30) | 2.22 | 2.15 |
| | Post | 30 | 90%(27/30) | 90%(27/30) | | | | |
| B/Massachusetts/02/2012 Ether | All | 60 | N/A | N/A | | | | |
| | Pre | 30 | 100%(30/30) | 67%(20/30) | 27%(8/30) | 23%(7/30) | 2.55 | 2.52 |
| | Post | 30 | 100%(30/30) | 73%(22/30) | | | | |
| B/Brisbane/60/2008 | All | 60 | N/A | N/A | | | | |
| | Pre | 30 | | | 7%(2/30) | 10%(3/30) | 1.50 | 1.48 |
| | Post | 30 | | | | | | |
| B/Brisbane/60/2008 Ether | All | 60 | N/A | N/A | | | | |
| | Pre | 30 | 87%(26/30) | 90%(27/30) | 13%(4/30) | 13%(4/30) | 1.64 | 1.55 |
| | Post | 30 | 97%(29/30) | 97%(29/30) | | | | |

FIG. 31

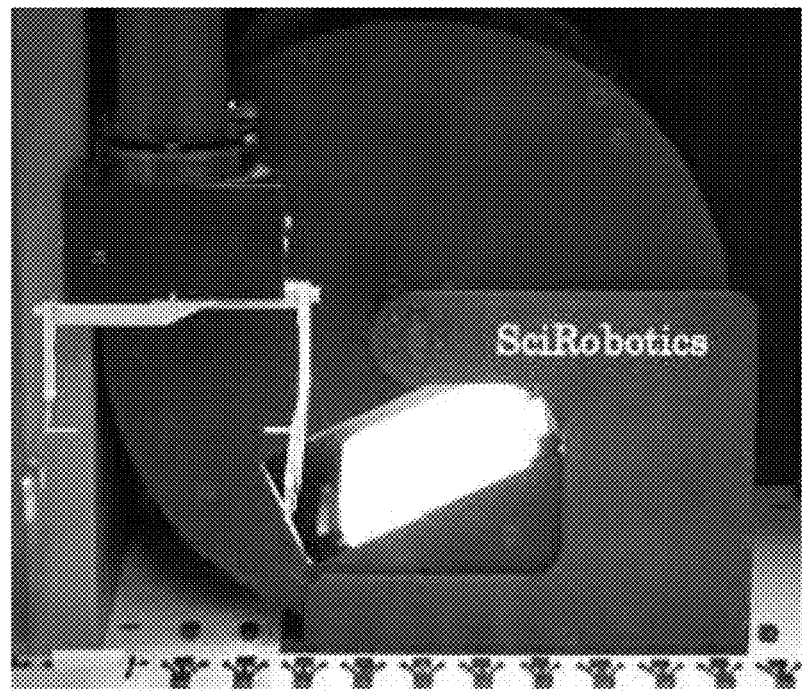
FIG. 34
(Conventional)

AUTOMATED IMAGING AND ANALYSIS OF THE HEMAGGLUTINATION INHIBITION ASSAY (HAI)

BACKGROUND OF THE INVENTION

The Hemagglutination Inhibition Assay (HAI) was developed over 70 years ago as a means to measure influenza-specific antibody levels in serum. The HAI has since been applied to many other hemagglutinin-containing viruses such as rubella, measles, mumps, parainfluenza, adenoviruses, polyomaviruses and arboviruses, to name a few. Currently, the HAI is recognized as the so-called gold-standard serologic test for typing influenza antibodies in humans and animals and it is widely used in influenza surveillance and vaccine testing.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 8 shows an automated HAI (HIVE) automated imager, in accordance with embodiments of the invention;

FIG. 28 is a table showing concordance results for an imager according to an embodiment of the invention as compared to a manual test;

FIG. 29 is a table showing additional concordance results for an imager according to an embodiment of the invention as compared to a manual test;

FIG. 30 is a table showing concordance results for a HIVE T670 imager embodiment of the invention as compared to a manual test;

FIG. 31 is a table showing additional concordance results for a HIVE T670 imager embodiment of the invention as compared to a manual test;

FIG. 34 shows a conventional imager system.

Throughout the drawings, like reference numbers should be understood to refer to like elements, features and structures.

DESCRIPTION OF EXEMPLARY EMBODIMENTS

Flu HAI is a pivotal serology test that supports many, if not all, Flu vaccine initiatives. Currently this classic assay is performed manually and meets all regulatory expectations. With increasing testing requirements, there is a need to improve the efficacy and throughput of flu HAI systems and methods, whether used in the context of influenza or other hemagglutinin-containing viruses.

The HAI is a 3 day assay typically performed in 96-well u- or v-bottom micro-titer plates. On day 1, nonspecific inhibitors are eliminated from the test sera by treating with a neuraminidase solution and incubating in a water bath for approximately 18 hours. On day 2, the sera samples are heat inactivated and agglutinins are adsorbed from the sera using red blood cells (RBCs). After a 2-hour incubation period at 2° C. to 8° C., the RBCs are removed through centrifugation. On day 3, titration of the influenza antigen of interest is performed to ensure a target value of 4 HAU/25 µL for use in the HAI assay. Once the antigen titer is verified, the treated sera samples are serially diluted and combined with the antigen. Serum-only, that is, no antigen present, control wells are also established at this point for later use as a gauge for the optimal read time. After a 1-hour incubation at 37° C. (±2° C.) or at ambient temperature, depending on virus strain, an RBC suspension is added to the samples and controls.

Figure 1:
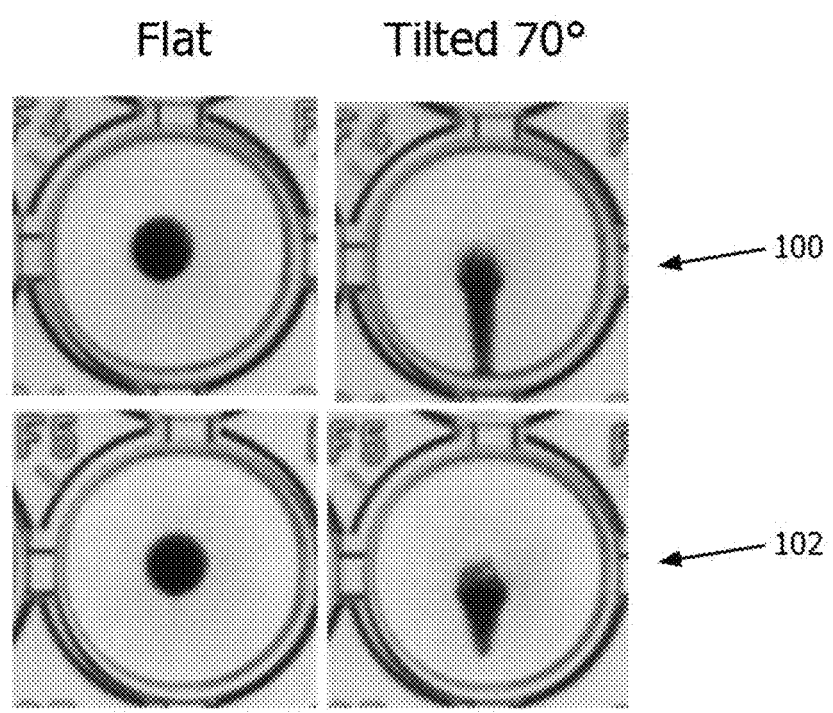
FIG. 1 illustrates the difference between HAI RBC Patterns when the plate is flat and when the plate is tilted, in accordance with embodiments of the invention.

After the RBC suspension is added, the samples are then incubated for 1-hour at ambient temperature. Following this incubation, the sample plate is gently tilted 60° to 70° and the agglutination state is recorded for each sample dilution once the RBC control well stream produces a "foot" pattern. A negative result flows at the same rate as the RBC controls, that is, complete streaming implies no agglutination, and has clear supernatant. This condition is illustrated by the image in the top-right quadrant 100 of FIG. 1. A positive result does not flow at the same rate as the RBC control due to hemagglutination. This condition is illustrated by the image located in the bottom-right quadrant 102 of FIG. 1. The HAI titer is assigned as the reciprocal of the highest serum dilution that exhibits complete inhibition of hemagglutination.

Traditional HAI techniques are performed manually, that is, by human lab technicians or other personnel specially trained to observe the plates after titration and render a determination of the results on each well of the plate. One of the main drawbacks of performing the classical HAI manually is the subjectivity of the visual readout. Titer assignments often vary among analysts depending on how or when the RBC patterns are interpreted. The fast kinetics of the streaming RBCs make it difficult for analysts to read all of the samples on a plate at the optimal time. Furthermore, analyst-to-analyst variation and bias can lead to inconsistent results and the need to re-test samples.

Also, HAI plates are typically not imaged during development and are discarded after they are read. Titer values are recorded manually and the raw data (RBC patterns) are destroyed during the course of the assay, thereby eliminating the possibility for other analysts to review the data post-assay. Standard, manual readout HAI technology is also not suitable for high-throughput analyses, where it would be necessary to handle a large number of plates within an allotted amount of time and keep track of when to read the plates. For example, a typical run of 36 96-well HAI plates must be evaluated by a single analyst in less than an hour. The plates are normally tilted 3 at a time and visually monitored while also minding a stopwatch. Once the optimal read time is reached, the titers are determined and recorded, the plates are discarded and the analyst moves on to the next set of 3 plates. With the increased volume of HAI testing required, this situation has become problematic.

There has been at least one known attempt to provide an automated HAI imager but this system is plagued by at least some of the problematic issues associated with manual testing. Referring to FIG. 34, this known system is the FluHema™ imager system offered by SciRobotics of Kfar Saba, Israel. The FluHema™ system develops and images one HAI plate at a time, that is, from top-down, and then performs image analysis to identify positive and negative wells. This system was designed for use with a Tecan Freedom EVO® lab automation platform. As a result, the throughput of the FluHema™ system is still unsatisfactory to address current needs. Also, due to higher distortion, non-telecentric imaging optics employed by the FluHema™, the efficacy of the system is also not ideal.

U.S. Pat. No. 8,962,256, which is incorporated herein by reference in its entirety for all that is taught, discloses a significantly more sensitive version of the HAI assay than was previously known. The HAI assay disclosed in the '256 patent is based on observing agglutination on activated surfaces of specifically opsonized plates and ELISA plates rather than in solution. Specifically, according to the '256 patent a method referred to as the Surface-Assisted Hemagglutination/Hemagglutination Inhibition functional assay, or "SA-HAI," is disclosed. The SA-HAI is for the functional characterization of viruses and virus-specific antibodies and sera. The sensitivity of the SA-HAI assays to various influenza viruses was found to be 7-200 times higher than the traditional HA assay, and sensitivity of the SA-HAI assay to influenza-specific antibodies 7-50 times higher than in the traditional HAI, depending on the types of viruses and erythrocytes used. The SA-HAI is typically evaluated using imaging technology, though it is imaged only one well at a time.

There is a need, therefore, for a more robust HAI testing methodology that has increased throughput over conventional methodologies and also provides a more consistent and reliable result.

To address the issues described above, and possibly others as well, with respect to manual HAI testing systems and the limited available automated systems, embodiments of the present invention provide an imaging solution for HAI testing that includes unique hardware and software components. Particular embodiments of the present invention image multiple plates at a time, optionally from the bottom-up, and employ low distortion telecentric imaging optics.

Exemplary embodiments of the HAI imaging solution disclosed herein include a standalone system that eliminates analyst subjectivity by automating the assay readout using computer vision and image processing and automatically assigning titer values for any sample, independent of the virus strain of interest or RBC species. Particular embodiments of the invention may be adapted for use with a multitude of different pathogenic viruses, including adenoviruses, enteroviruses, reoviruses, myxoviruses, poxviruses, and flaviviruses, which cause a wide spectrum of human and animal illnesses, from influenza and rubella to smallpox and Dengue hemorrhagic fever. Similarly, embodiments of the invention may be adapted for use with RBCs from various species. For example, in accordance with WHO recommendations, turkey, chicken and horse RBCs may be tested in v-bottom places that are tilted for imaging, while guinea pig and human type 0 RBCs may be tested in u-bottom plates and imaged while flat. A system consistent with one or more embodiments creates an archive of HAI plate images to serve as raw data that can be evaluated post-assay, all with a throughput capability that exceeds manual analysis.

As mentioned, embodiments of the invention disclosed herein include both hardware and software components. The following provides an overview of examples of each of these individual components.

Various embodiments include several different imagers and system configurations. The different imagers according to one or more of these embodiments are referred to herein as prototypes as they were developed initially for proof of concept and to acquire the initial data for tuning the image processing algorithm discussed later. Some of the key areas of focus for the various imagers include the optical train and the plate handling system, with one of the more important general aspects being a fully automated imager. General, but non-limiting, system requirements for an automated imager consistent with preferred embodiments of the invention include, (1) process up to 100 plates per hour; (2) tilts assay plates at a 70° angle; (3) integrate with standard plate stacker; (4) full-plate imaging for true kinetic analysis; (5) real time image processing for immediate analysis and titer determination; and (6) small footprint, that is, the imager fits on standard lab bench.

Several prototype imagers were developed in accordance with various embodiments; some of these prototypes are outlined below.

Figure 2A:
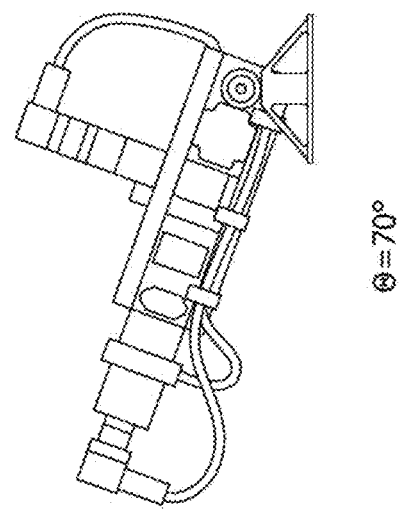
FIGS. 2A-2C show an imager at varying degrees of tilt, in accordance with embodiments of the invention.
Figure 2B:
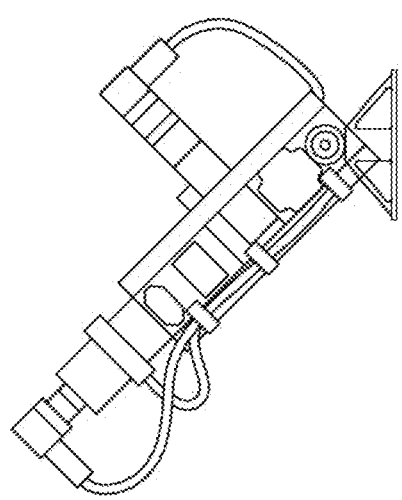
Figure 2C:
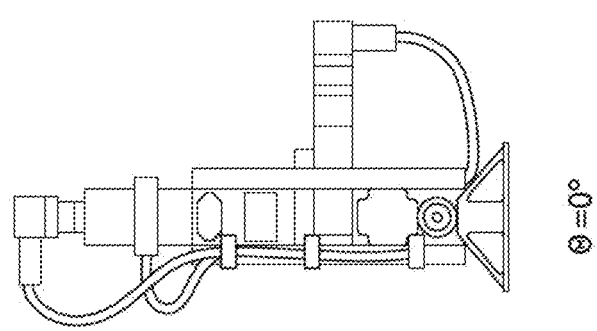

A prototype 1 imager, shown in FIGS. 2A-2C, resembles an imager developed previously for SA-HAI, but with various important modifications. In particular, this imager comprised an X-Y stage for plate positioning with respect to a 1.3 megapixel camera which was attached to a Z-stage for focusing. Also, a rotation stage was added to the imager to allow for automated tilting from 0° to 70°. FIG. 2A illustrates the imager tilted 0°, FIG. 2B illustrates the imager tilted 45°, and FIG. 2C illustrates the imager tilted 70°. This imager also is preferably integrated into an automation line and accessible by robotic arm.

The prototype 1 imager had two issues when imaging HAI plates. First, the camera was only capable of single well imaging and it took approximately 1.5 minutes to image an entire 96-well plate. Due to the fast RBC pattern development kinetics, this relatively slow imaging was not considered ideal for titer determination from the image. Second, the HAI plate was illuminated in an epi-illumination configuration which created significant glare from reflection off of the bottom of the plate that complicated image analysis.

Figure 3:
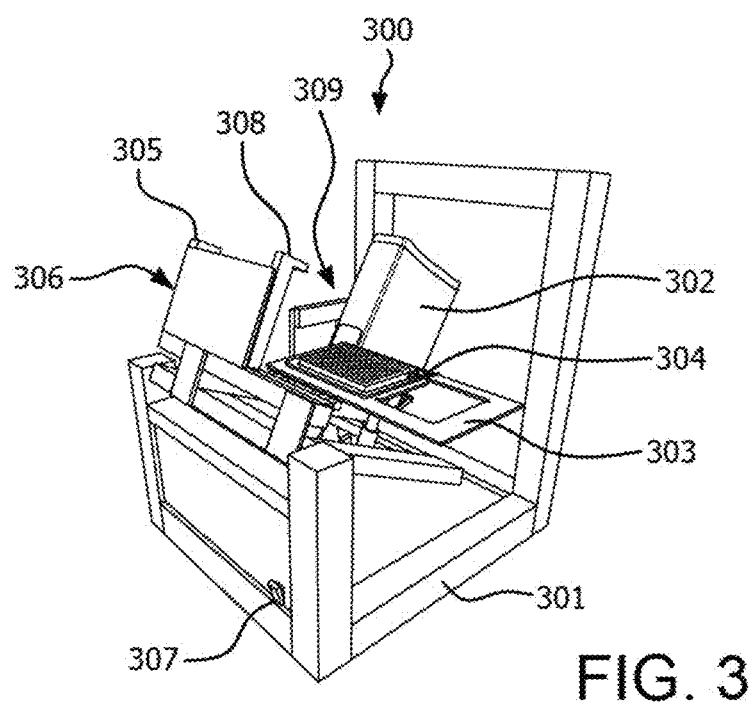
FIG. 3 shows an imager, in accordance with embodiments of the invention.
Figure 4:
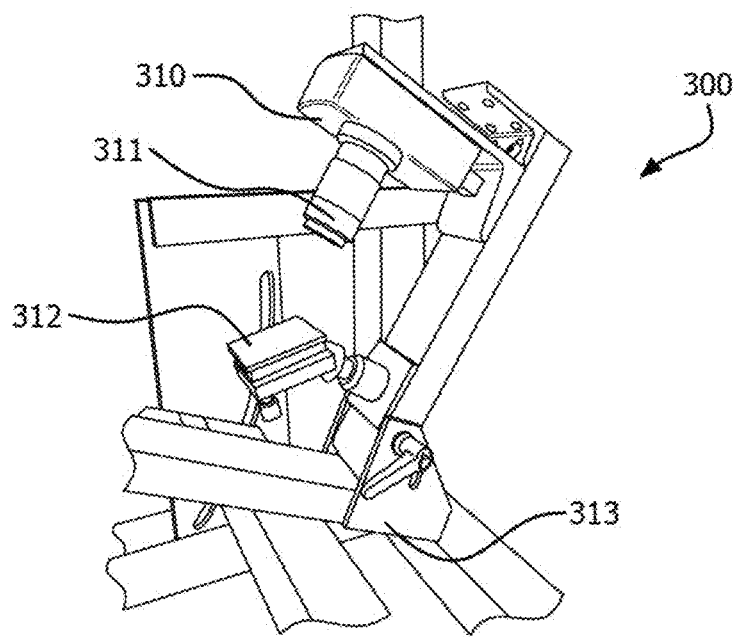
FIG. 4 shows further detail of the optics portion of the imager shown in FIG. 3, in accordance with embodiments of the invention.

Referring to FIGS. 3 and 4, a prototype 2 imager improves on the shortcomings of prototype 1 by improving the imaging optics and implementing full-plate imaging. It uses a high f-number lens to image the entire plate in a single snapshot while attempting to minimize distortion. The camera is at least a 5 megapixel CMOS sensor to provide higher resolution for image processing. The plate is illuminated via an LED backlight in a trans-illumination configuration rather than epi-illumination to avoid reflections. The imager is loaded manually by locking a plate on a slide assembly and then rotating the assembly into the imaging plane at 70°. Kinetic imaging is simultaneously triggered on a PC running custom image acquisition software.

As illustrated in FIG. 3, the prototype 2 imager 300 comprises a frame 301 upon which an imaging assembly 302 and a slide assembly 303 are mounted. Slide assembly 303 includes a plate holder 304 for holding a 96 well plate. The imager 300 includes a magnetic lock 305 and a backlight 306. An on/off switch 307 is provided to power on and off the imager 300. The imager includes an assembly guide 308 to maintain the slide position with respect to the backlight 306. The imager 300 also includes an angle adjustment mechanism 309 for adjusting the angle of the imaging assembly 302. Referring to FIG. 4, the imager 300 imaging assembly 302 comprises a high resolution imaging CCD 310, a 16 mm HR lens 311, and a reflection mirror 312. A tilt adjustment 313 for the optical path is also provided. The imaging assembly 302 provides variable axis imaging in order to reduce shadowing and lensing effects associated with plate media.

Figure 5:
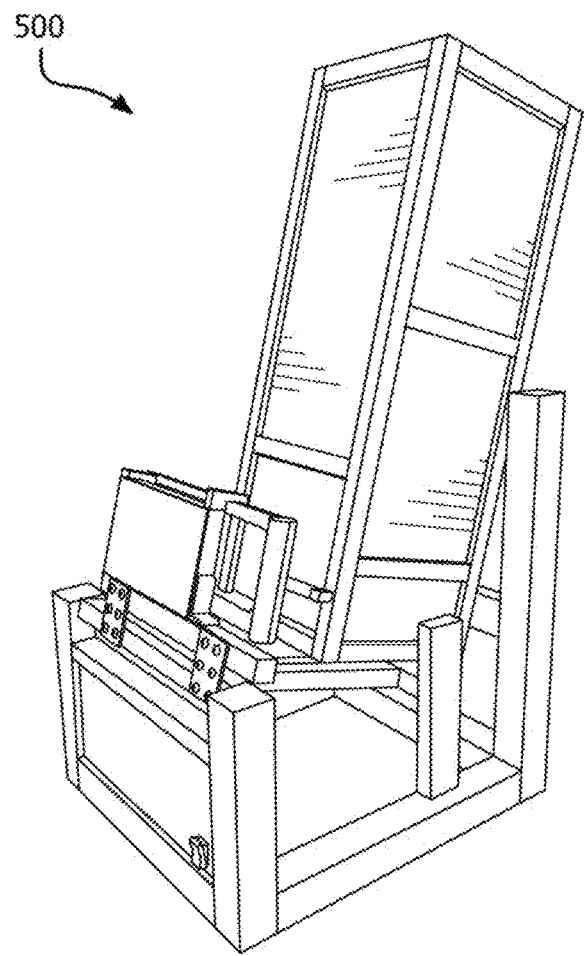
FIG. 5 shows another imager, in accordance with embodiments of the invention.
Figure 6:
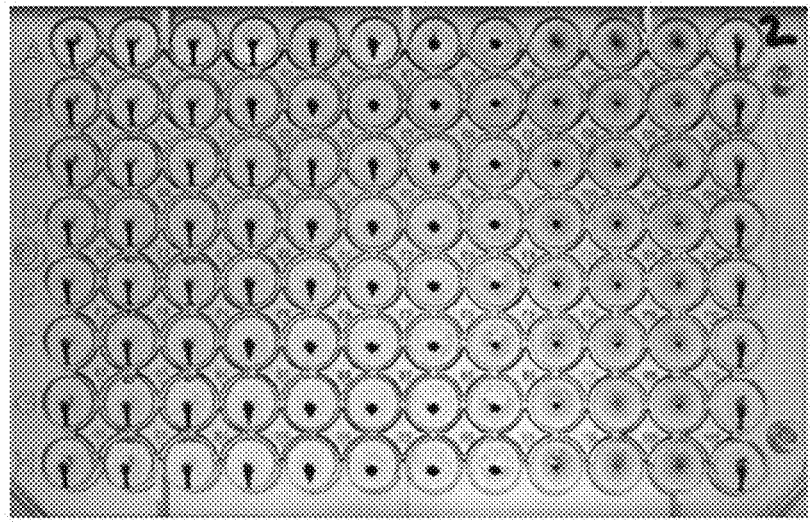
FIG. 6 shows compact lens distortion and shadowing around edges with a trapezoidal effect top to bottom for a 96-well plate in accordance with embodiments of the invention.
Figure 7:
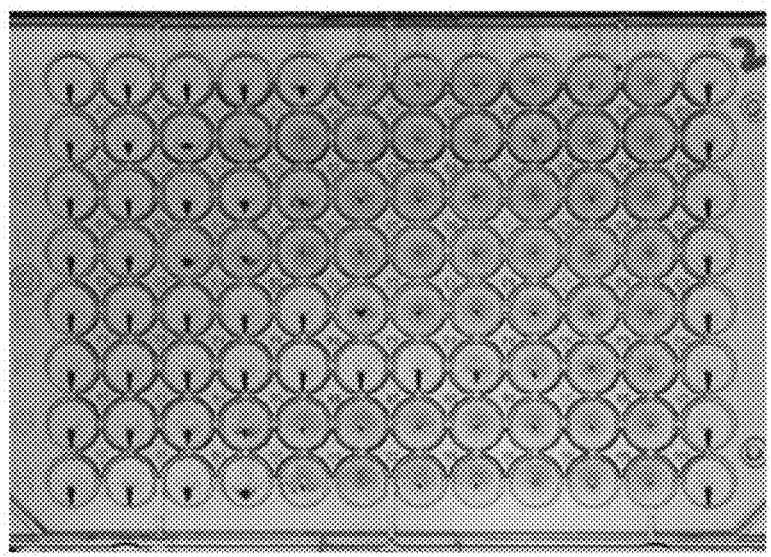
FIG. 7 shows how a telecentric lens reduces distortion and shadowing of the a plate image, in accordance with embodiments of the invention.

With respect to prototype 3 500, which is shown in FIG. 5, the imaging optics on prototype 2 were replaced with a large format telecentric lens and 5 megapixel CCD sensor to improve image quality. For example, FIG. 6 illustrates compact lens distortion and shadowing around the edges resulting in a trapezoidal effect top to bottom. Referring to FIG. 7 it is shown that the addition of the telecentric lens reduced the distortion and shadowing and proportions were maintained across the plate. HAI data was generated using both manual and automated reading methods/algorithm for four influenza antigens covering different Influenza types and subtypes and the results showed concordance.

Building on each of the prior prototypes a preferred embodiment is the HIVE T670, or simply, HIVE. "HIVE" stands for High-Throughput Imaging and Visualization Equipment and "T670" refers to the ability to tilt 6 plates simultaneously at 70 degrees. Referring to FIG. 8 the HIVE 800 is an instrument capable of fully automated, high-throughput kinetic imaging of HAI plates. The HIVE combines high-resolution, low-distortion telecentric imaging with fully automated plate handling including tilting to any desired angle. RBC development and imaging is preferably conducted at tilt angles substantially close to 0° and/or 70°. Further, the HIVE is compatible with many different types of industry standard automated plate handlers, such as robotic arms, stackers and cranes.

Figure 9A:
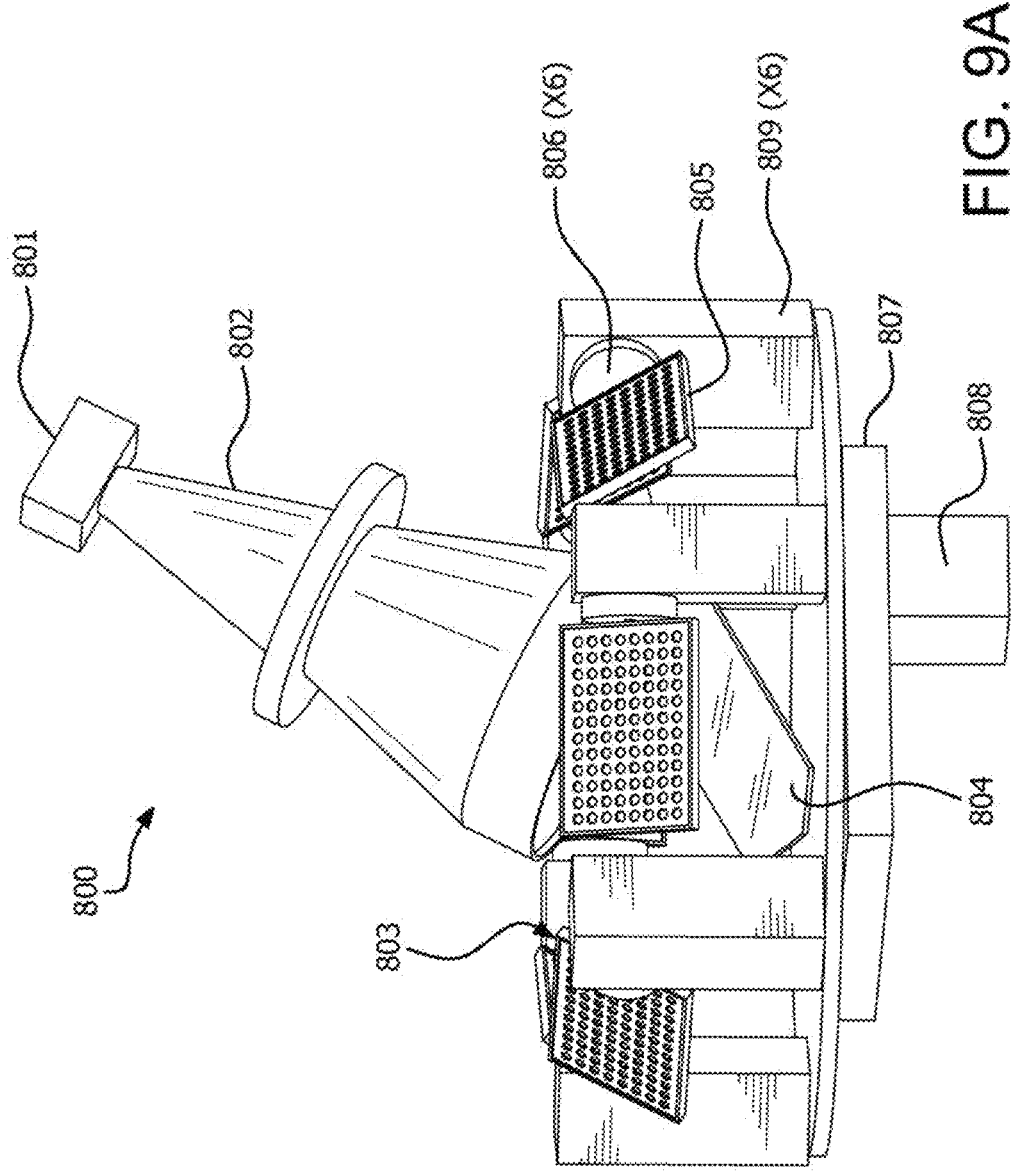
FIG. 9A shows the various internal components of a HIVE automated imager, in accordance with embodiments of the invention.

Next, the optics of the system hardware will be discussed. More particularly, and referring to FIG. 9A, the HIVE imager 800 images HAI plates using a high-resolution CCD camera 801, preferably having a 5 or 11 megapixel resolution, attached to a telecentric lens 802 that provides a low distortion image with minimal parallax error and sufficient field-of-view to encompass the entire plate. According to one or more embodiments the plate is imaged from the bottom while the plate is tilted, such as at 70°, and transilluminated by a highly uniform LED backlight 803. An adjustable turning mirror 804 is positioned between the lens and the HAI plate to reduce the overall footprint by folding the optical path.

With respect to plate handling, the HIVE has six (6) individually addressable, rotation stages 806 controlled by motor 809 with tilting plate holders 805 mounted to a motorized rotating carousel 808 that cycles plates from a load/unload position to an imaging position and back. A slip ring 807 provides electrical connections between the rotating carousel 808 and the static base of the HIVE. According to the embodiment shown in FIG. 9A, the HIVE 800 includes a high resolution CCD camera 801, for example, 5 megapixels, mounted above a custom plate holder 805 and is equipped with a telecentric lens 802. All motion and camera operations are controlled via the image acquisition software component of the graphical user interface, or GUI, described in further detail later. The HIVE processes up to six plates simultaneously and the throughput for the automated imager is about 100 plates per hour, or 50 plates in a single unattended run, when coupled, for example, to a BioTek BioStack™ NEO micro-plate handler, assuming a typical plate development time of about 120 seconds and approximately a 30 second imaging window.

Figure 9B:
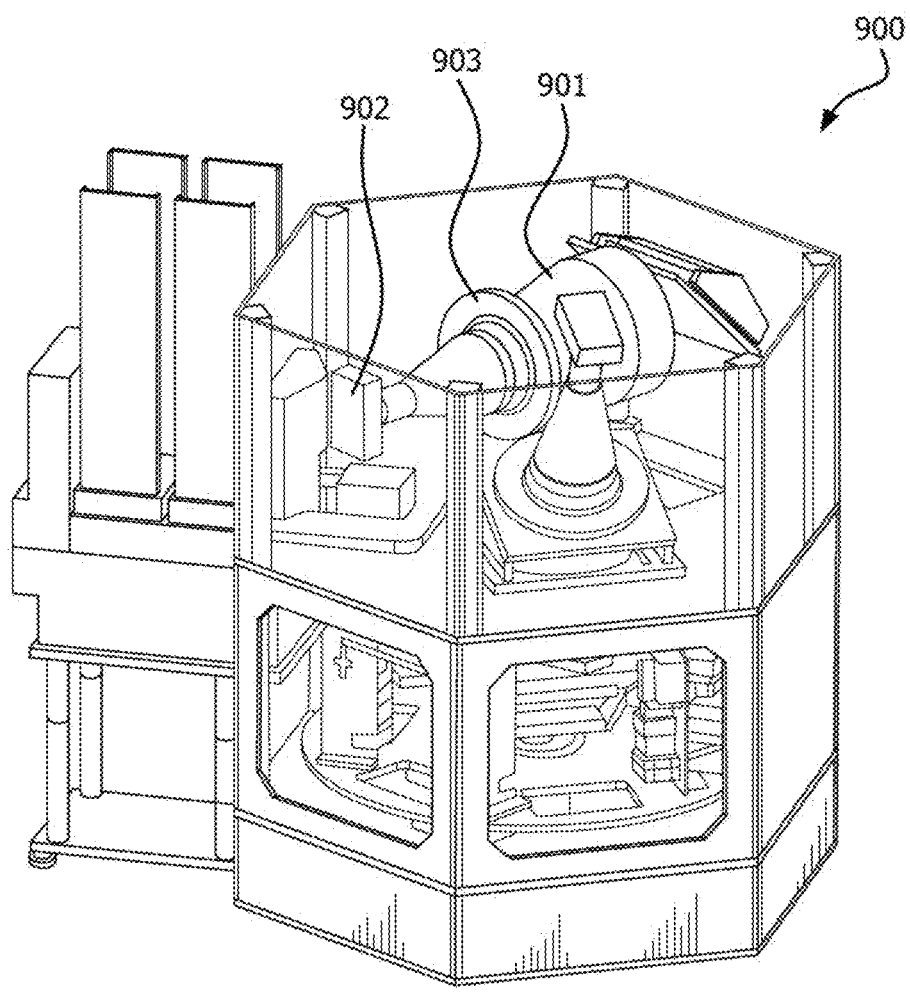
FIG. 9B shows a HIVE Dual Mode automated imager, in accordance with embodiments of the invention.

Referring to FIG. 9B, the HIVE Dual Mode imager 900 expands the capability of the HIVE T670 with the addition of a second optical train 901 for imaging plates without tilting (that is, at substantially 0°). The optics comprise a high-resolution CCD camera 902 and telecentric lens 903 for 0° whole-plate imaging at the carousel rotation position prior to the 70° imaging position. A second LED backlight below the plate provides trans-illumination similar to 70° imaging. The camera 902 and telecentric lens 903 may be mounted vertically above the 0° imaging position, or perpendicular to the imaging plane with the addition of a turning mirror to fold the optical path. The HIVE Dual Mode imager 900 processes up to three hundred plates per hour in flat (0°) imaging mode, or 50 plates in a single unattended run, when coupled, for example, to a BioTek BioStack™ NEO micro-plate handler. The throughput for the tilted imaging mode is identical to the throughput for the HIVE T670, that is, 100 plates per hour under normal assay conditions. Applications for the HIVE DM include the HAI assays that are typically read without tilting, for example, those which use guinea pig or human type 0 RBCs, as well as the Surface-Assisted HAI (SA-HAI). The HIVE DM can also be used to image plaque assays and others which are performed in SBS titer plates in various well formats (including but not limited to 6-, 12-, 24-, 48-, 96-, 384-, 1536-, and 3456-wells) that are assessed using a visual readout. In a preferred embodiment, the 0° imaging optical train has a higher resolution CCD camera than the 70° optical train, for example 11 megapixels, to accommodate the wide range of possible assay types. It should be understood that the identity of the red blood cells (RBCs) that may be used in the apparatus and methods of the present invention are not limited by the source of the cells. For example, RBCs from mammalian species including human, cat, dog, mouse, rat, guinea pig, horse, sheep, pig and the like may be used. Similarly, cells from avian species including turkey, chicken and the like, may be used. The blood isotype corresponding to the RBCs used in the apparatus and methods of the present invention are also not limited. For example RBCs from human blood types A, B, AB and O may be used.

The software component of various exemplary embodiments of the invention will now be described. In particular, the software component is comprised of two main sub-components, the image processing algorithm and the graphical user interface. The image processing algorithm automatically determines sample titer values and the graphical user interface integrates the image processing algorithm with the imaging, motion and data management controls.

Figure 10:
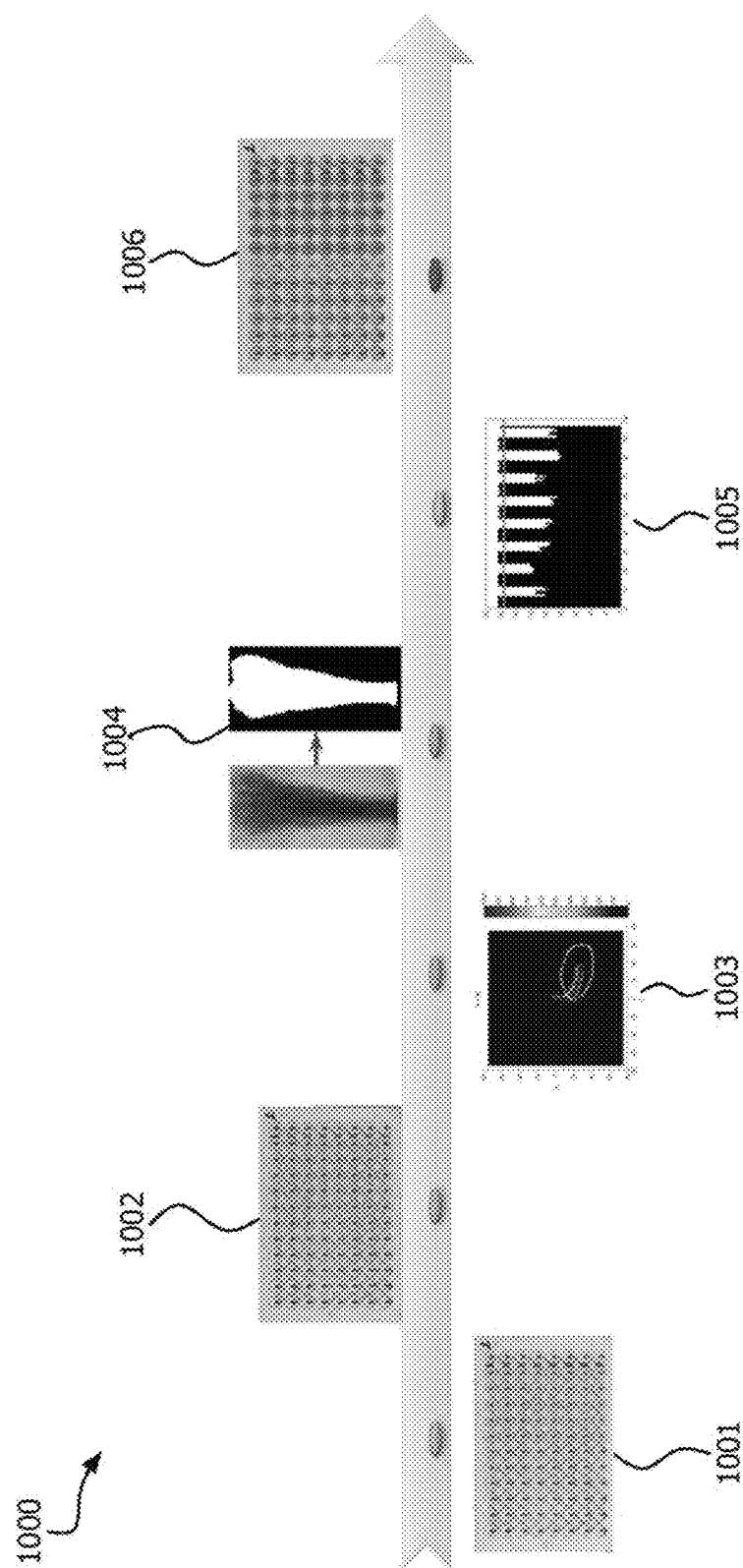
FIG. 10 is a flow diagram associated with an image analysis algorithm, in accordance with embodiments of the invention.

Regarding the image processing algorithm, HAI titer plates are imaged as a whole, either looking top-down into the wells or looking bottom-up through the wells, in order to capture the state of all RBC well patterns at the same moment in time. Further, as controlled by the software, tilted HAI plates are often imaged at multiple time points during their development cycle, such as, every 10 seconds beginning at 90 seconds post tilting to 120 seconds post tilting, in order to capture the RBC streaming kinetics. The image processing algorithm must find and evaluate each individual well in the whole-plate image and determine its agglutination state. Once the agglutination states are determined for each well on the plate, titer values are assessed for the corresponding samples. FIG. 10 shows a sequential timeline 1000 for various process steps in the image analysis algorithm in accordance with embodiments of the invention. The first step 1001 is loading an image, and flipping the image if the image was bottom imaged. The next step 1002 is to define a well mask using auto-triangulation or from stored measurements. The next step 1003 is to apply global L*a*b segmentation. In the next step 1004, the image analysis algorithm loops through each well, and defines ROI, segments and measures. In the next step 1005, the algorithm classifies wells based on measurements. The classifications preferably include agglutinated, non-agglutinated, titers, and outliers. At step 1006, the image analysis algorithm creates a plate image overlay showing well classifications, and saves the data, such as in an SQL database.

Figure 11:
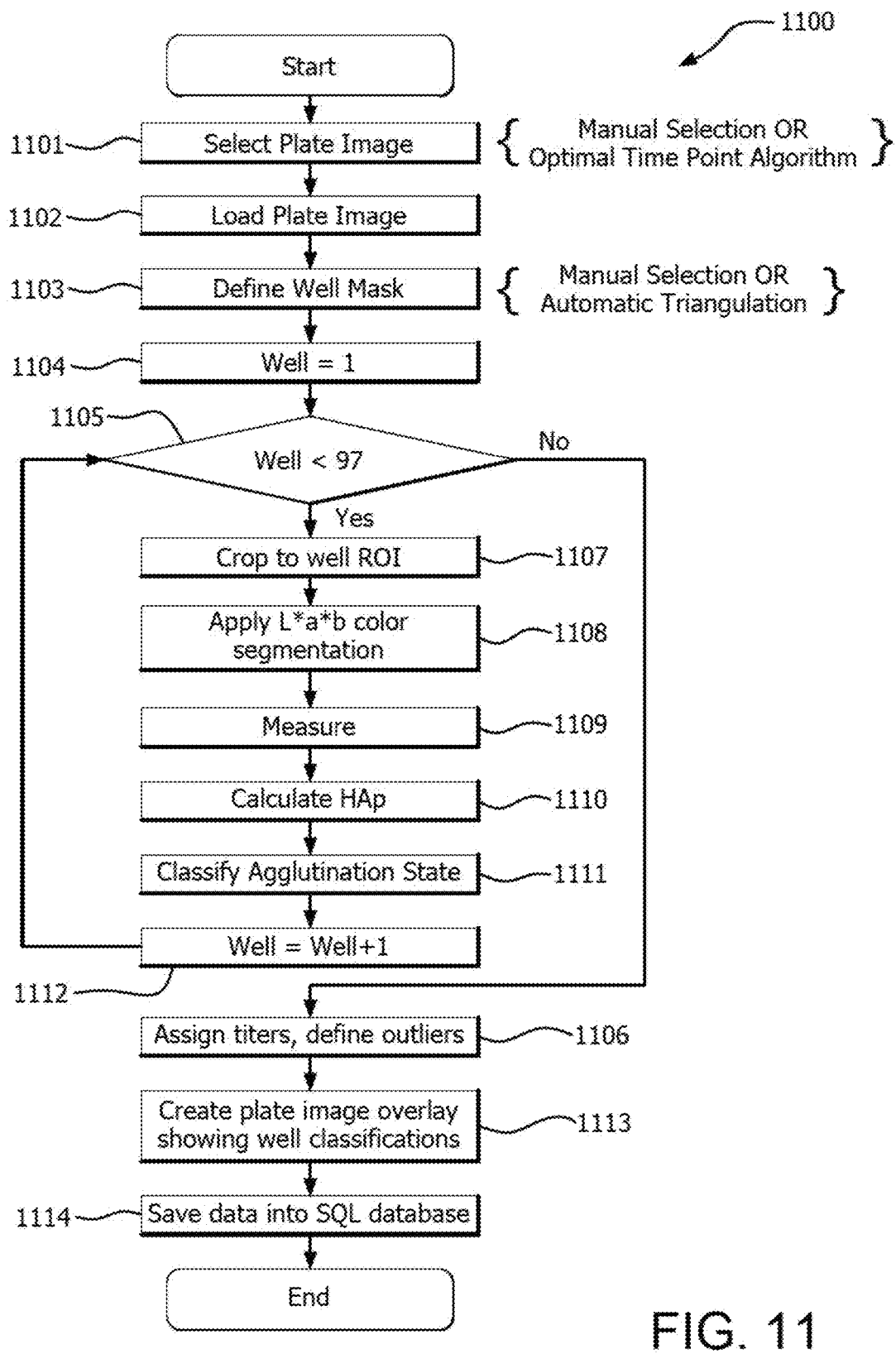
FIG. 11 is a flow chart illustrating the processes associated an automated HAI imager, in accordance with embodiments of the invention.

More detailed information regarding HAI image processing according to exemplary embodiments is illustrated in the flow chart 1100 of FIG. 11. As shown, the first step 1101 is to select the image, that is, plate, for processing. Typically, HAI plates are imaged at multiple time points during their development cycle, such as after tilting, in order to capture the RBC streaming kinetics. The image to be analyzed must be selected from this collection of kinetic images either manually or using an algorithm that selects the image that was acquired closest to the optimal read time. Manual selection is accomplished by highlighting the plate image of interest from a table of images in the database. As discussed in more detail below, the optimal time point algorithm automatically determines the optimal image using image processing to analyze and compare the control well patterns to a reference pattern. Once the image is selected, it is loaded into the image processing algorithm at step 1102. Since this is a full-plate image, the next step 1103 is to define a well mask that locates all of the individual wells that need to be processed in the image.

There are two modes for defining the well locations, that is, a manual mode where a user defines the well location, and an automatic mode where a further algorithm is employed using, for example, triangulation techniques. The manual mode depends on the user to interactively define the centroids and radii of certain specific wells, for example, wells A1, A12 and H12 for a 96-well plate, by aligning a circle with their outline on the plate image. All other well centroids are then calculated from these three points.

At step 1104, the well number is set to 1. At step 1105, the algorithm checks to see if all of the 96 wells in the plate have been processed. If all of the wells have been processed the method continues to step 1106. If there are still wells to be processed then the method continues at step 1107, in which the image is cropped to the well region of interest (ROI). At step 1108, L*a*b color segmentation is applied. At step 1109 several features of the RBC pattern are measured. These features preferably vary as a function of agglutination state. At step 1110 a hemagglutination parameter is calculated. At step 1111 the well is classified according to agglutination state. At step 1112, the well number is incremented and then the method loops back to step 1105.

At step 1106, the method assigns titers and defines outliers. At step 1113, the method creates a plate image overlay showing the well classifications. At step 1114, the data is saved, such as to an SQL database.

The automatic well definition algorithm applies the same principle, but uses image analysis to find the centroids. Further detail regarding the well definition algorithm is provided below. After the locations of the wells are determined, the next step is to iteratively process each of the well RBC patterns and determine their agglutination state. The general steps for processing the well patterns according to embodiments of the invention are, (1) crop the image to a region of interest containing the RBC pattern, (2) convert the RGB image to L*a*b* (Lab) color space, e.g., as defined by CIELAB where dimension L indicates lightness and a and b represent the color-opponent dimensions, based on nonlinearly compressed CIE XYZ color space coordinates, and apply a pre-defined gate that segments the RBC pattern from the rest of the image, and (3) measure several features of the RBC pattern that vary as a function of the agglutination state. These are derived from image moments and include the length of the RBC stream (L), the location of the bottom-most pixel (B) and the weighted centroid in the Y-axis (Y). After these measurements are taken, the hemagglutination parameter is calculated in accordance with EQN. 1.

$$HA_P = L*B*Y \quad \text{(EQN. 1)}$$

The hemagglutination parameter ($HA_P$) is then used to classify the well as either agglutinated or not agglutinated as discussed in detail later. After the agglutination states are determined for each well on the plate, the titer values are assigned for each sample dilution series as the reciprocal of the highest dilution which is non-agglutinated. If a sample dilution series exhibits outliers such as non-continuous agglutination states or invalid control wells, e.g., due to pipetting errors, the samples are flagged by the algorithm and a titer value is not assigned. Following titer assignment and outlier detection, a false-color plate image overlay is applied to visually depict the well classifications determined by the algorithm. All calculated values are then stored in a memory device in a format recognizable by one or more relational database programs for future retrieval.

Figure 12:
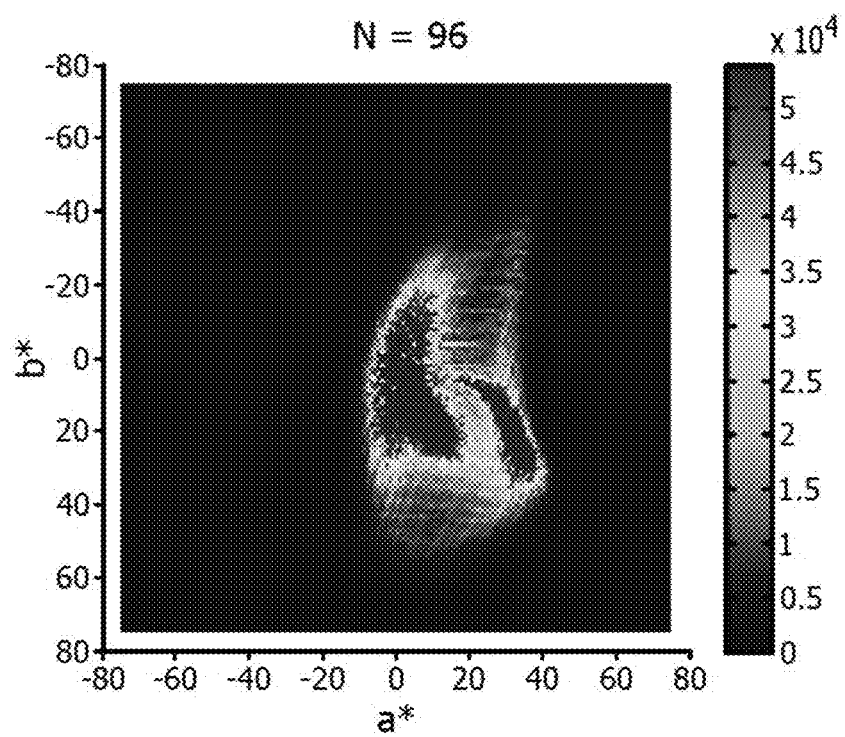
FIG. 12 is an L*a*b* colorspace map, in accordance with embodiments of the invention.

With respect to RBC pattern segmentation in L*a*b* color space mentioned previously, color segmentation is used to separate RBC patterns from the plate images. The original RGB image is first converted to L*a*b* color space and then compared to a pre-defined "gate." This color gate is defined manually by creating a composite L*a*b* color space gate from a large number, e.g., thousands, of wells and recording the location of the pixels which correspond to the RBCs. FIG. 12 illustrates an exemplary L*a*b* color space map in accordance with one or more embodiments of the invention. Once the gate has been defined, segmenting the RBC pattern is accomplished by discarding pixels which do not fall within the gate.

Optimal Time Point Algorithm

Figure 13:
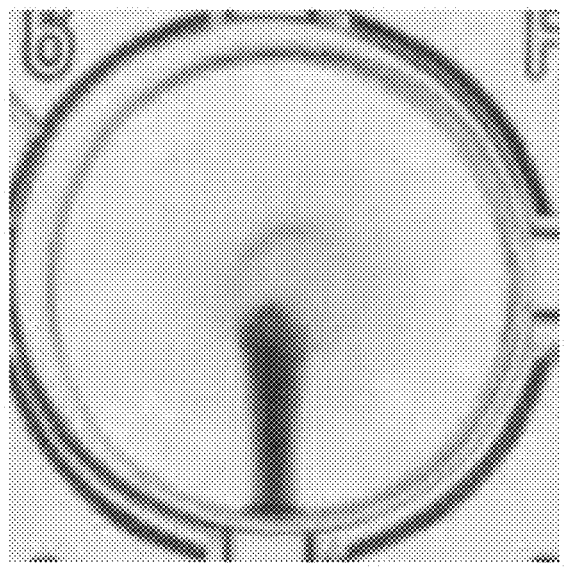
FIG. 13 is an RBC control well used during an image processing algorithm, in accordance with embodiments of the invention.

A goal of the optimal time point algorithm is to determine the optimal plate image from a collection of kinetic images acquired during plate development. According to at least one embodiment it accomplishes this by emulating an analyst observing the RBC control wells for the optimal read time, which is defined as the point at which the RBC control pattern has streamed to the bottom of the well and formed a 'foot', as shown for example in FIG. 13.

Figure 14:
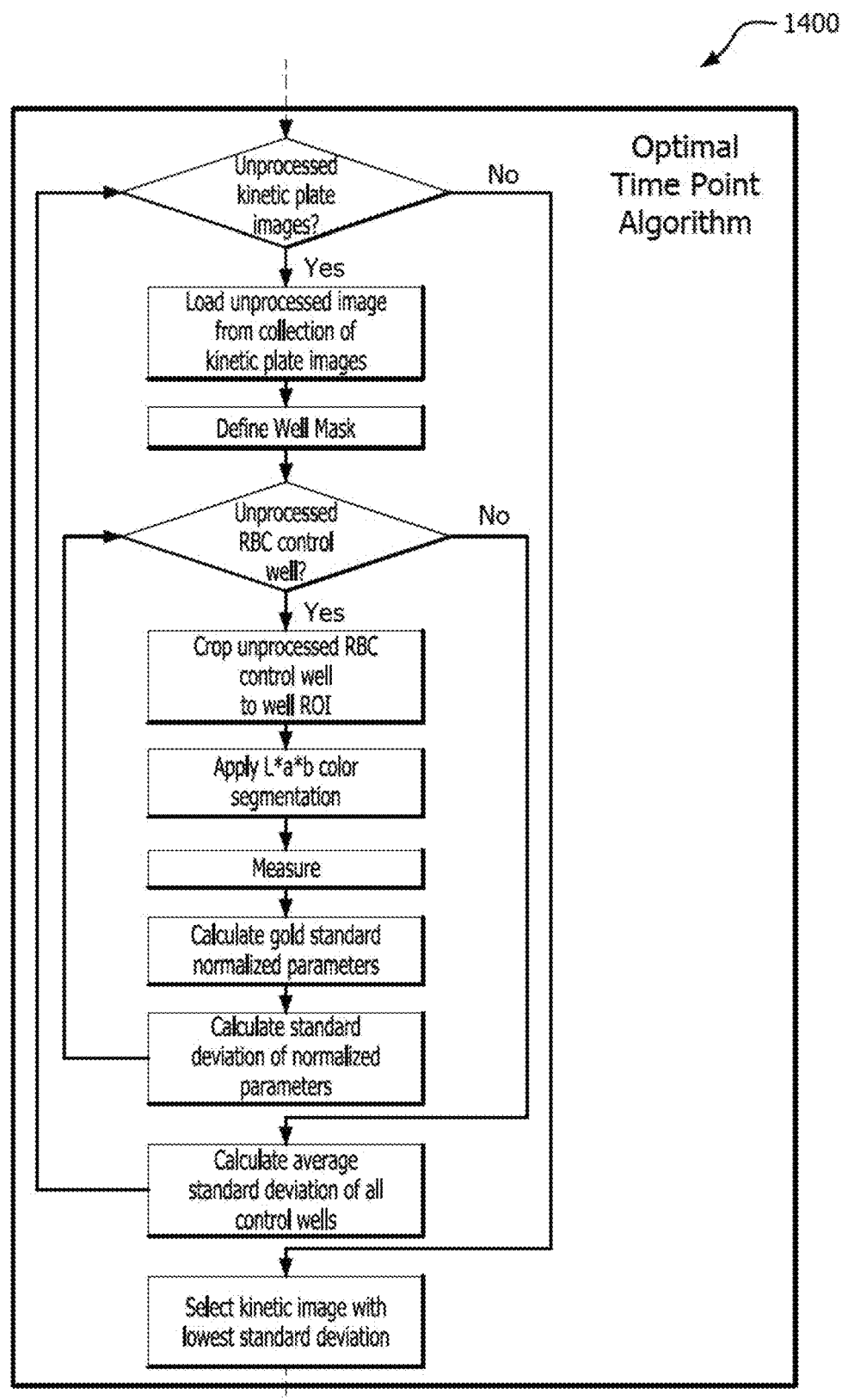
FIG. 14 is a flow chart illustrating an optimal time point algorithm, in accordance with embodiments of the invention.

The process 1400 of an exemplary time point algorithm according to at least one embodiment is illustrated in FIG. 14. As shown, the algorithm iterates through a collection of kinetic images for a selected plate and processes only the RBC control wells to determine the length of the RBC stream (L), the location of the bottom-most pixel (B), the area of the well (A), the perimeter (P), the equivalent diameter (D), the weighted centroid in the Y-axis (Y), and the circularity (C) for each RBC control. The measured values for each of these parameters are then normalized to reference parameters which are averages derived from the many, e.g., thousands, RBC control wells that have been selected manually as optimum. The rationale for this particular normalization scheme is that as a measured parameter approaches the reference parameter, the value of the normalized parameter, or more particularly their ratio, will approach unitary, that is, 1.

Figure 15:
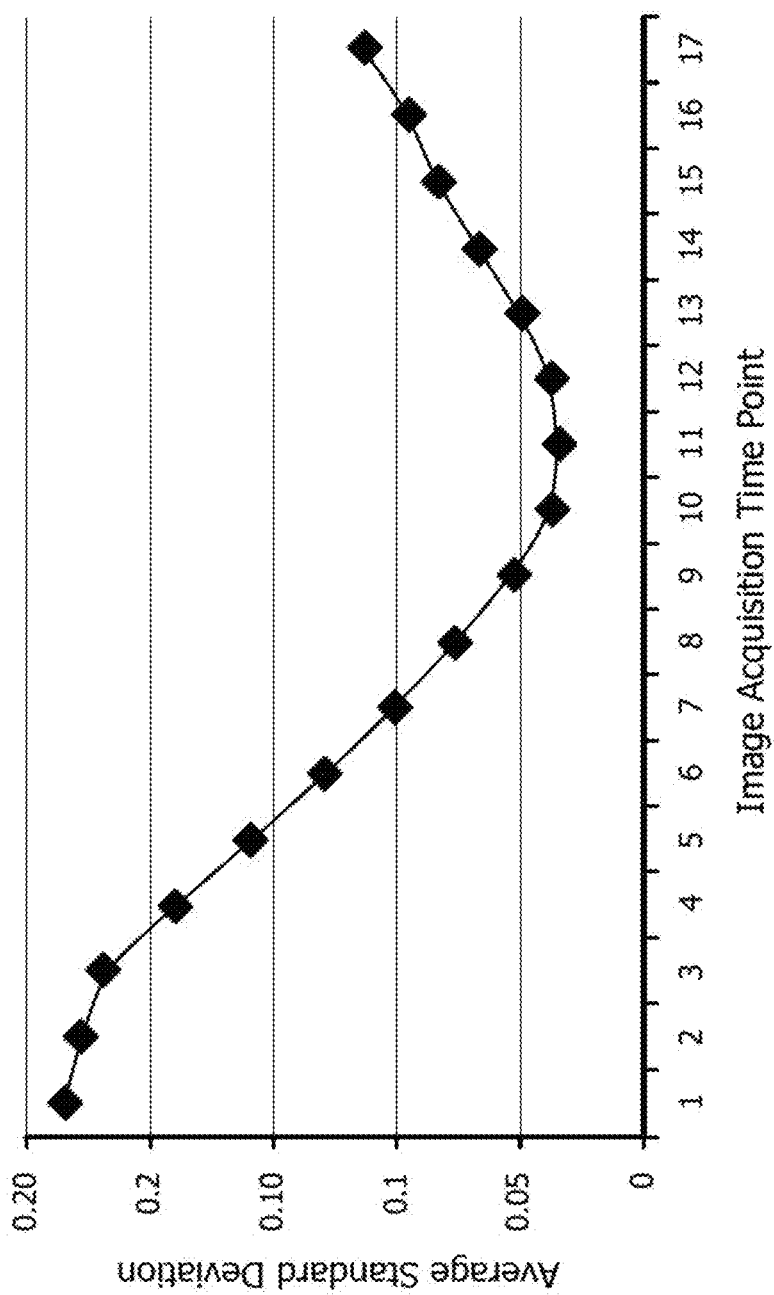
FIG. 15 is a chart showing average standard deviation versus image acquisition time, in accordance with embodiments of the invention.
Figure 17:
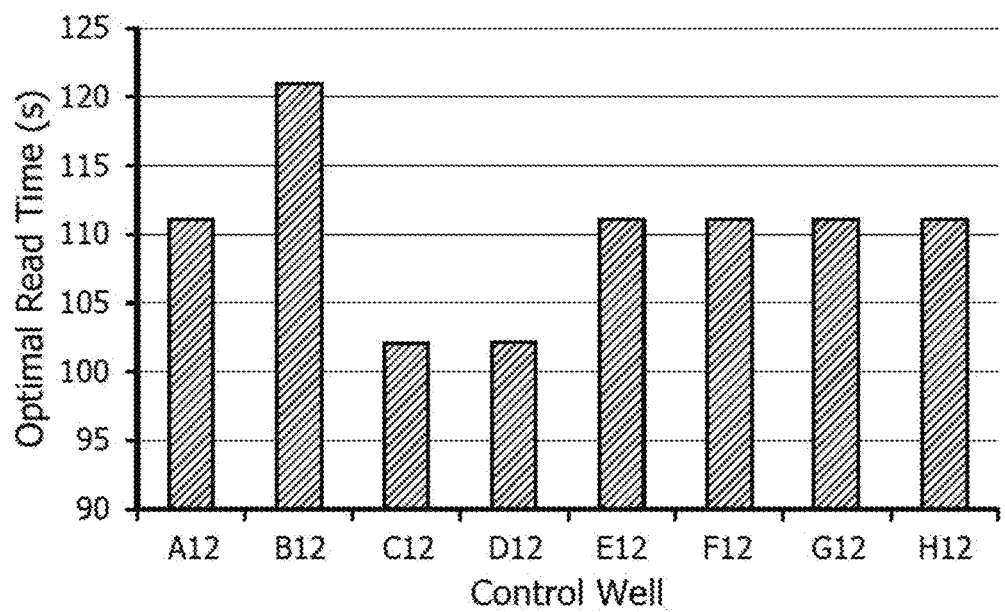
FIG. 17 is a chart showing optimal read time variation for a single plate, in accordance with embodiments of the invention.
Figure 18:
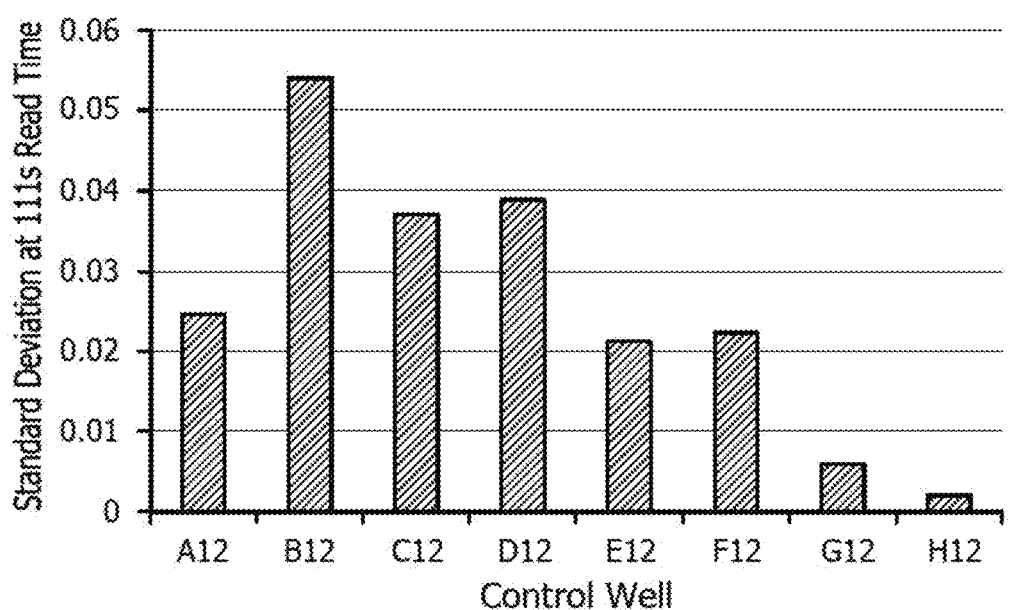
FIG. 18 is a chart showing standard deviation variation for single plate, in accordance with embodiments of the invention.

When all of the normalized parameters for an RBC control well are closest to 1, the pattern in that well is determined to be closest to the reference and therefore closest to the optimal read time. Since the values of all normalized parameters are nearly equal, e.g., they approach 1, at the optimal time point, the standard deviation of their values gives a single numeric indication of how close a given RBC pattern is to optimal. In general, RBC control wells within a plate will develop at slightly different rates due to normal experimental variations. For example, FIGS. 17 and 18 show the variation of the optimal read times and standard deviations respectively for eight RBC control wells on the same plate. In particular embodiments, the optimal read times are about 100 to about 125 seconds post tilting the plate from 0 degrees to 70 degrees. To evaluate the overall state of the plate, the average of all the standard deviation values is taken into account. The image with the lowest average standard deviation of RBC control well normalized parameters is therefore nearest the optimal time point. A typical average standard deviation versus time plot for RBC control wells is shown in FIG. 15.

Figure 16A:
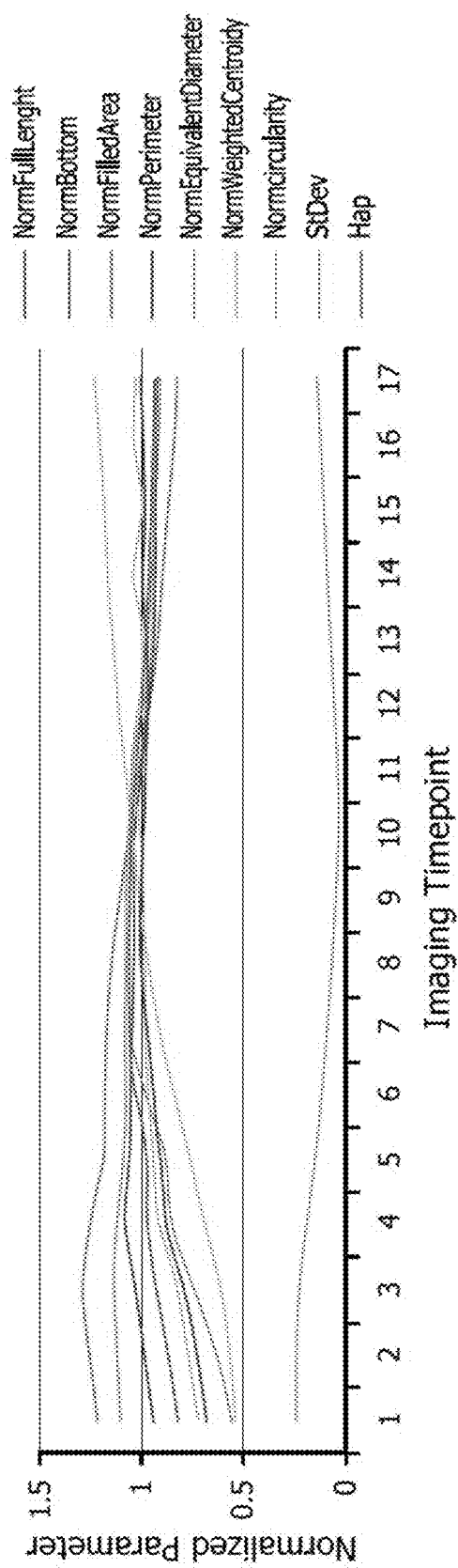
FIGS. 16A-16C are charts showing normalized parameters as a function of image acquisition time for different degrees of agglutination, in accordance with embodiments of the invention.
Figure 16B:
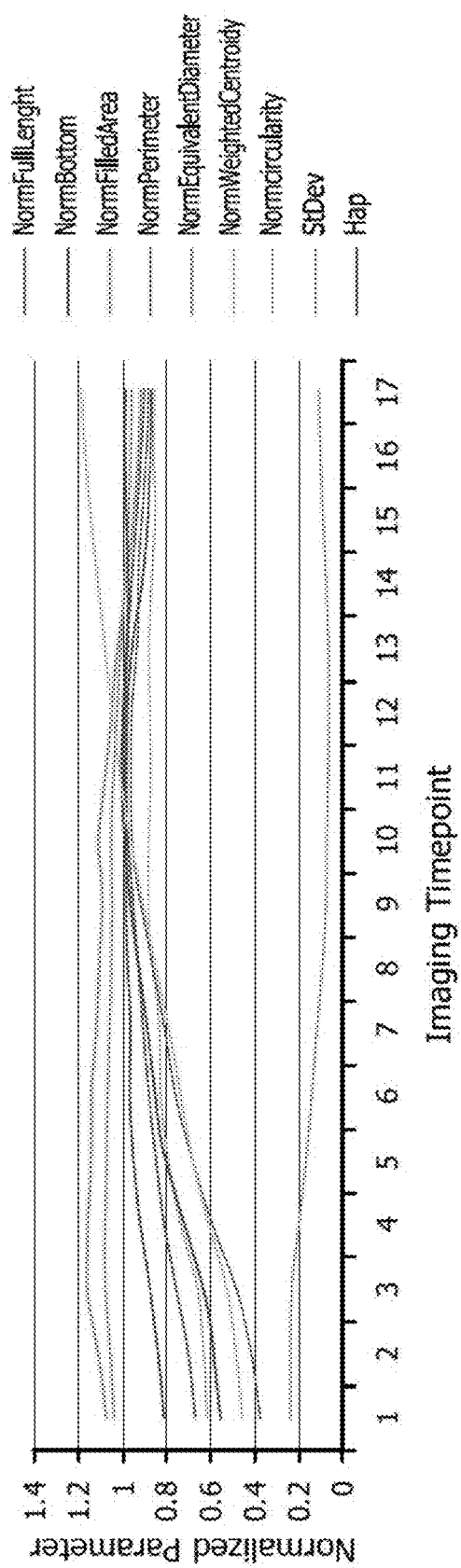
Figure 16C:
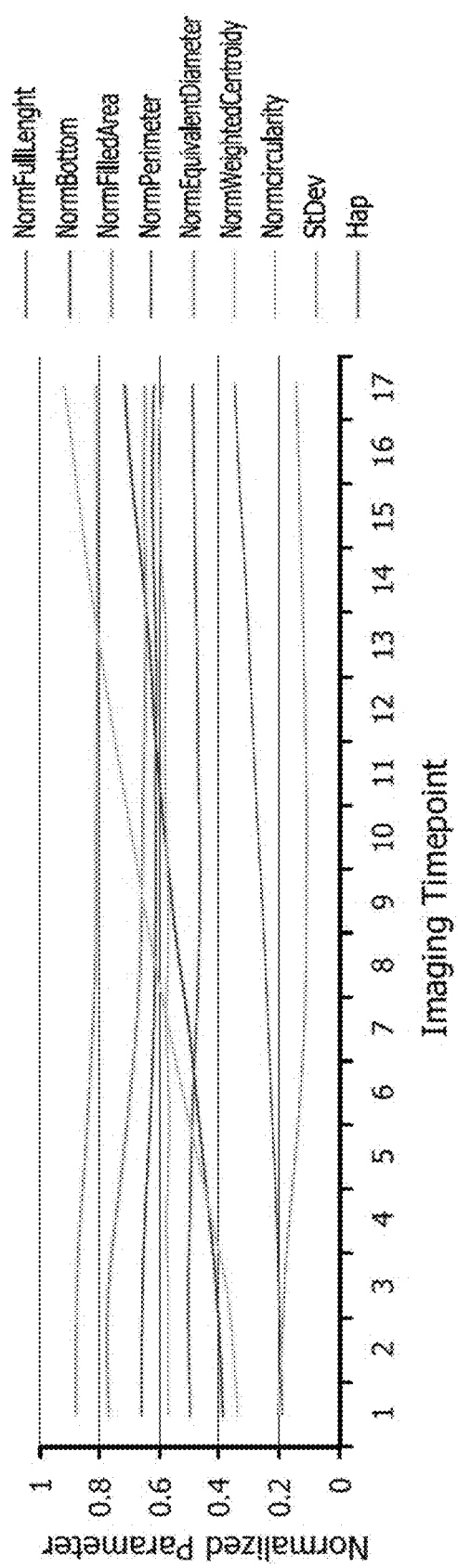
Figure 19A:
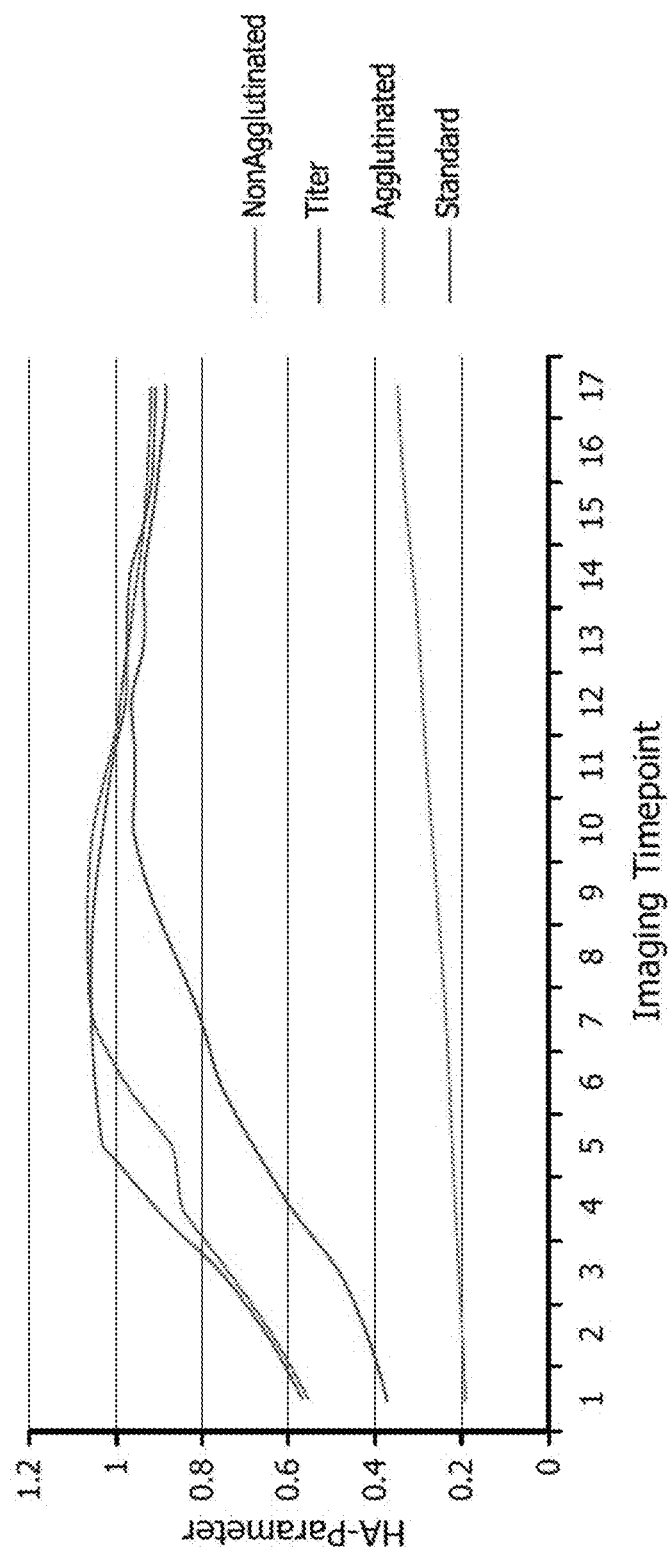
FIGS. 19A-19B are a charts showing parameter deviation as a function of time and agglutination state, in accordance with embodiments of the invention.
Figure 19B:
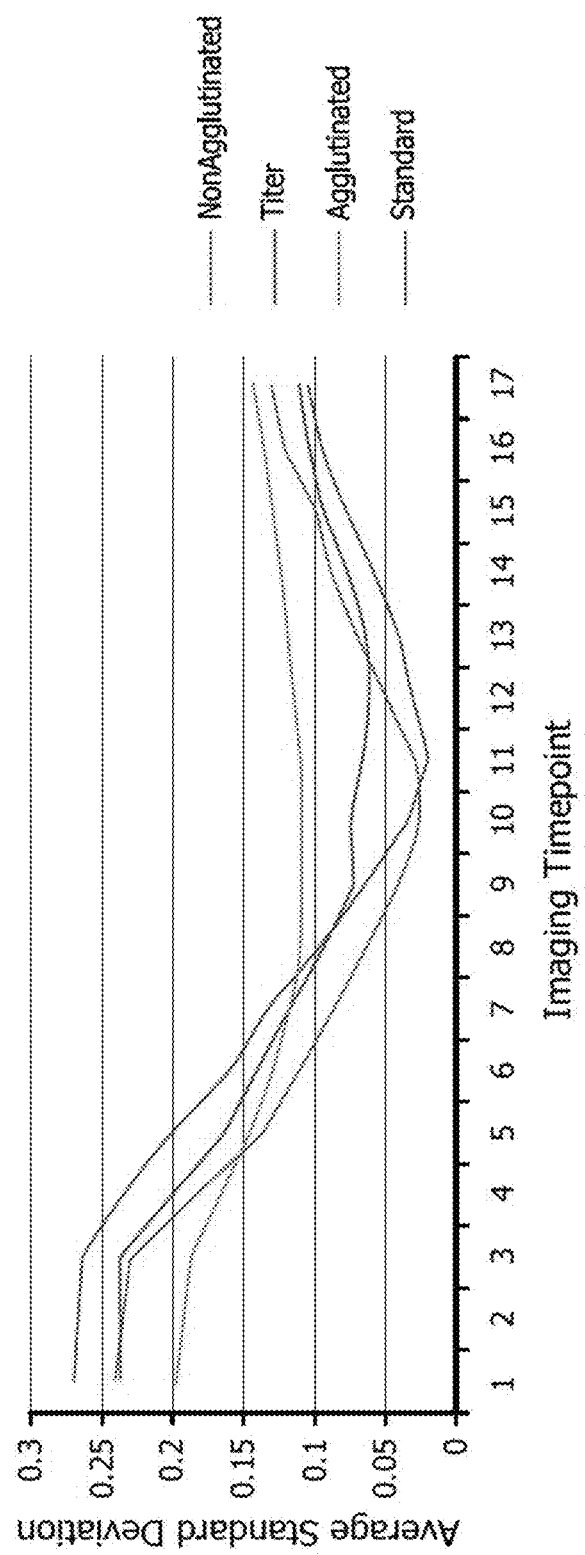

The behavior of the normalized parameters as a function of imaging time point is shown in FIGS. 16A-16C for three respective and different cases: non-agglutinated (FIG. 16A), agglutination onset (FIG. 16B) and agglutinated (FIG. 16C). As shown in FIG. 16A, the normalized parameters converge tightly to a value of 1 for the non-agglutinated case at an imaging time point of 100 seconds. This is due to a close match with the reference. The convergence of the normalized parameters is less pronounced for the case shown in FIG. 16B where agglutination is beginning to occur, and no convergence is observed in FIG. 16C for the non-agglutinated case. FIGS. 19A-19B show how other parameters, such as the HA-Parameter (as calculated by EQN. 1 above) and average standard deviation vary as a function of time and agglutination state.

Automatic Well Definition Algorithm

Figure 20:
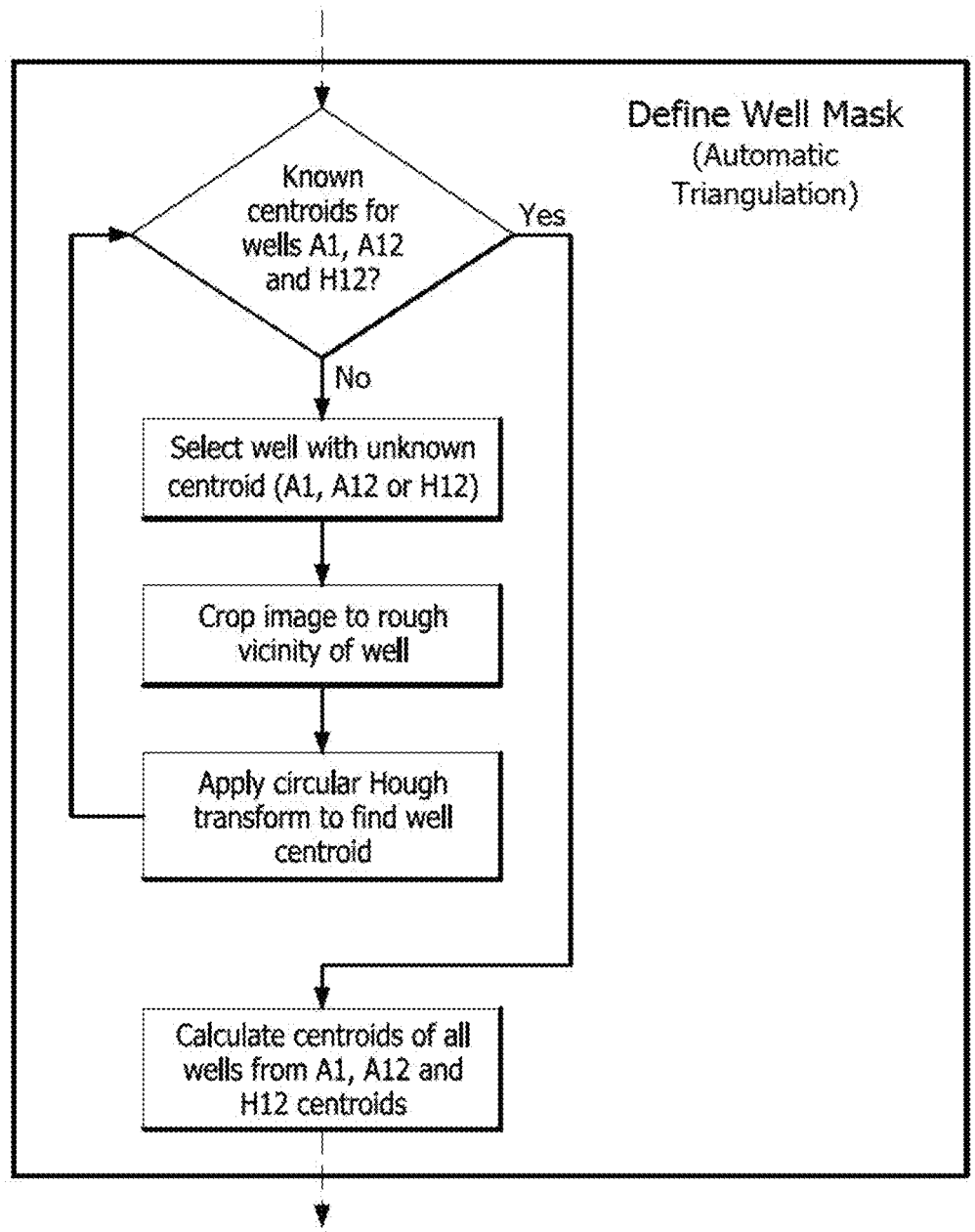
FIG. 20 is a flow chart illustrating an automatic well mask algorithm, in accordance with embodiments of the invention.

An automatic well detection algorithm according to embodiments of the invention is illustrated in FIG. 20. This algorithm iteratively calculates the centroids and radii of wells A1, A12 and H12, e.g., for a 96-well plate, through image analysis by applying a circular Hough transform to a region containing the well. The found centroids and radii are then used to calculate the positions of the remaining wells on the plate.

Agglutination State Classification Algorithm

Figure 21:
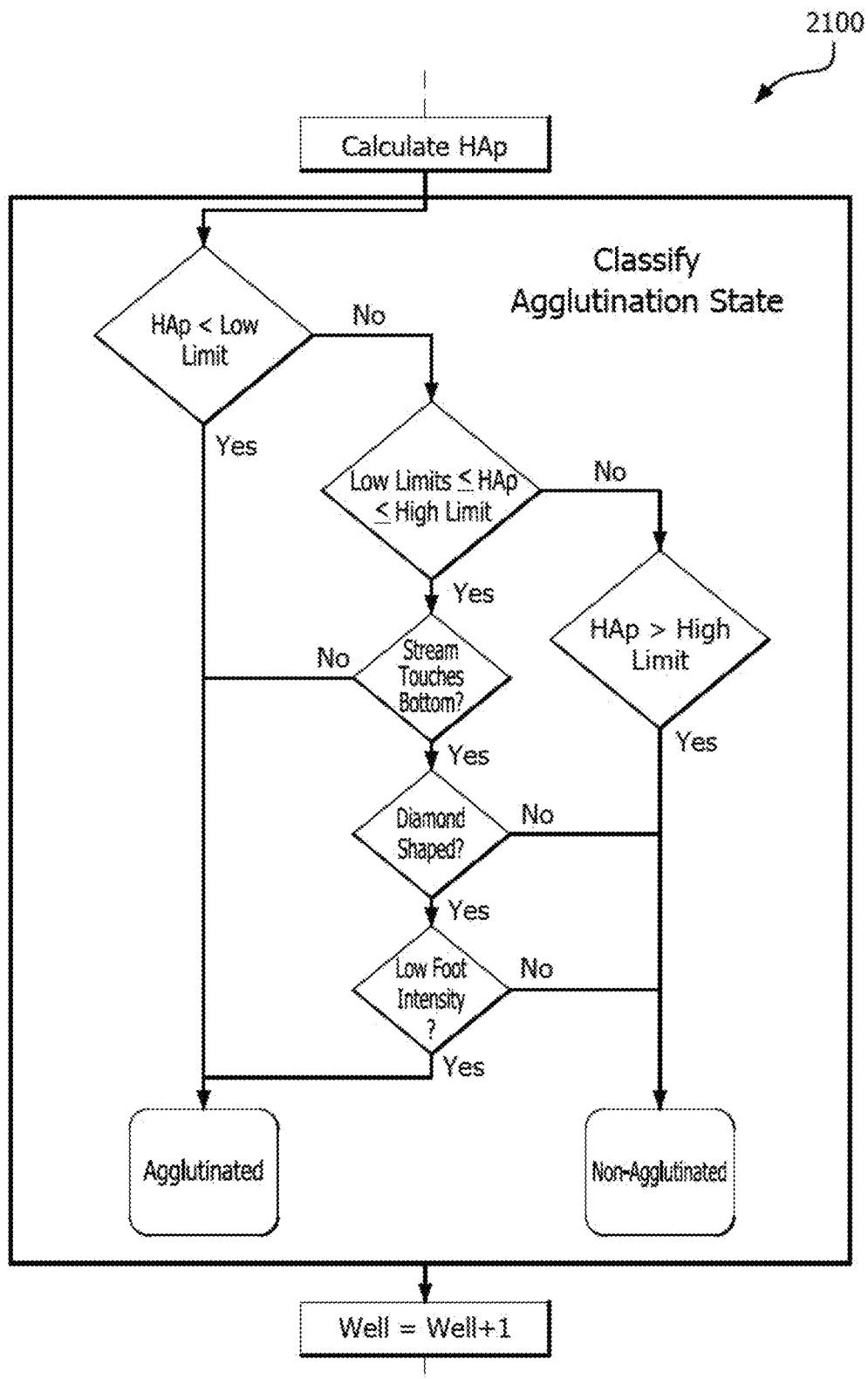
FIG. 21 is a flow chart illustrating an agglutination state classification algorithm, in accordance with embodiments of the invention.

According to embodiments of the invention the agglutination state is classified using the algorithm illustrated in the flow chart 2100 in FIG. 21. A well, according to the embodiment illustrated, is classified as either agglutinated or non-agglutinated. After calculating the HA-parameter, the classification algorithm determines where the HA-parameter lies with respect to pre-set limits. These pre-set limits are determined apriori from matching the numeric result with the manual analysis of many samples. If the HA-parameter is less than the lower limit, then the well is classified as agglutinated. If the HA-parameter is determined to be above the high limit, then the well is classified as non-agglutinated. If the value of the HA-parameter falls between the low and high limits, then additional analysis is conducted on the well pattern to determine its state.

Figure 22:
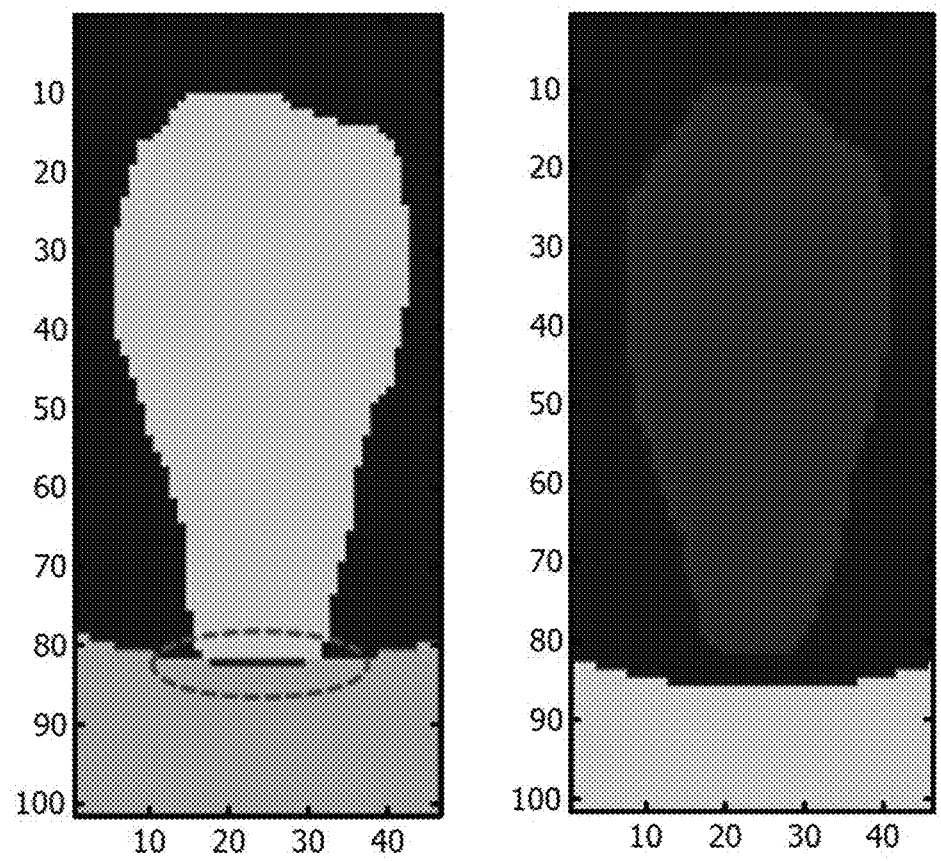
FIG. 22 illustrates edge detection for a foot pattern, in accordance with embodiments of the invention.

More particularly, additional image processing is initially conducted to determine if the RBC stream touches or overlaps the well wall. This determination is made by employing an edge detection algorithm, for example, as illustrated in FIG. 22. If overlap of the wall and the stream is detected, then the well is classified as non-agglutinated. Otherwise the well is classified as agglutinated. Subsequently, second order central image moments are compared against preset thresholds to determine if the RBC pattern exhibits a diamond shape. If the thresholds are exceeded, the well is classified as agglutinated. Finally, the pixels near the RBC pattern foot are examined to determine if the foot intensity is sufficient. Patterns with low foot intensity are classified as agglutinated.

Graphical User Interface (GUI)

Many, if not all, aspects of the automated imaging and analysis are integrated by the Graphical User Interface (GUI). The GUI according to the exemplary embodiments expressly disclosed herein is divided into three main areas: Image Acquisition, Image Analysis and Data Management, each of which is described in detail below.

Image Acquisition

The image acquisition component of the GUI according to one or more embodiments is responsible for acquiring whole-plate images at user-specified time points and saving the images along with their metadata in the relational database.

A run scheduler operates in conjunction with the image acquisition component. The scheduler takes user input on desired plate imaging kinetics such as development time, imaging window, imaging interval and number of plates and determines the optimal motion control operations to achieve the users request for a given number of plates. The schedule produced by the scheduler is used to control the motion and imaging hardware during an image acquisition run.

Figure 24:
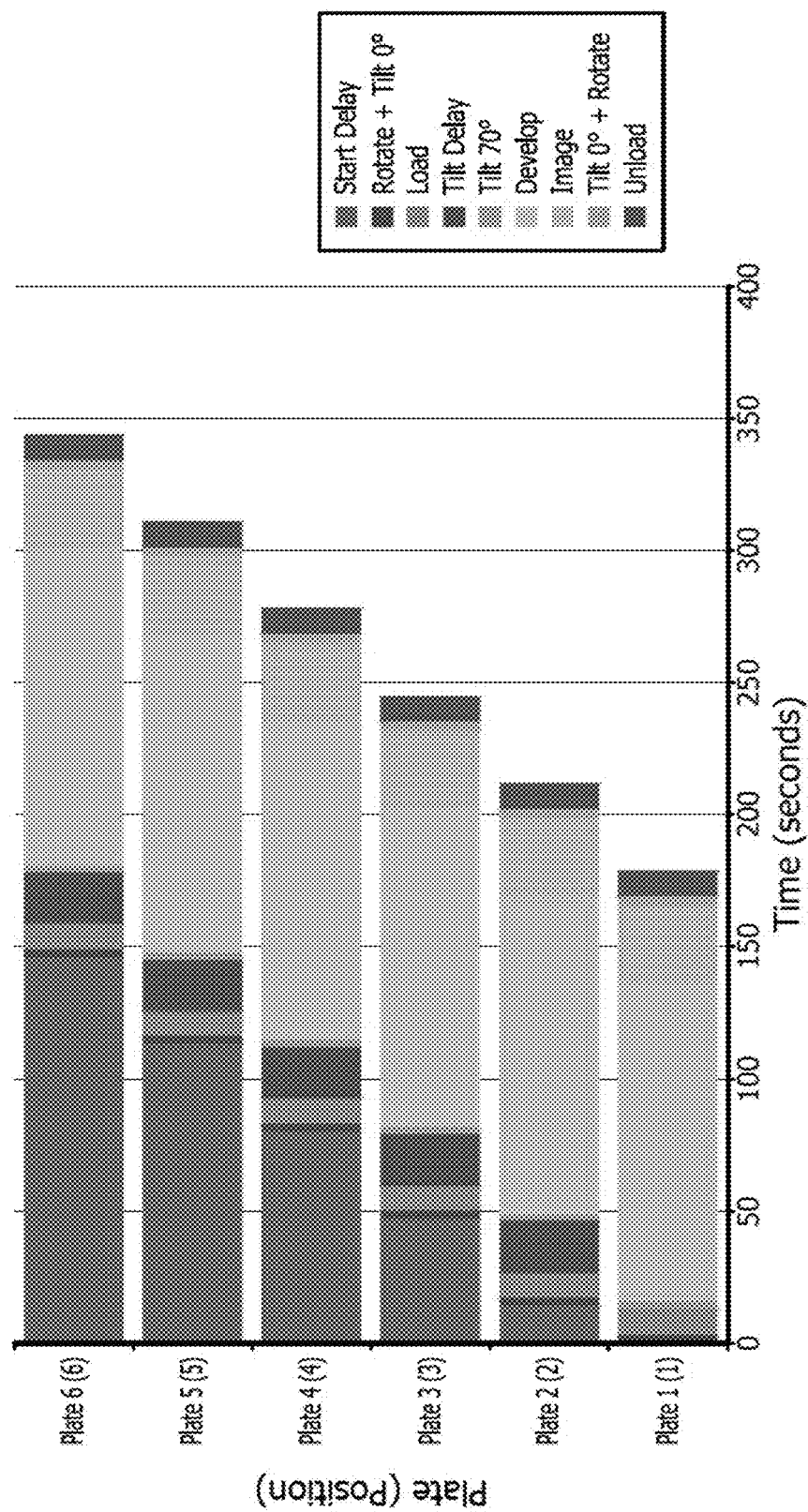
FIG. 24 is a timing diagram with respect to automated imaging of 6 plates, in accordance with embodiments of the invention.
Figure 25:
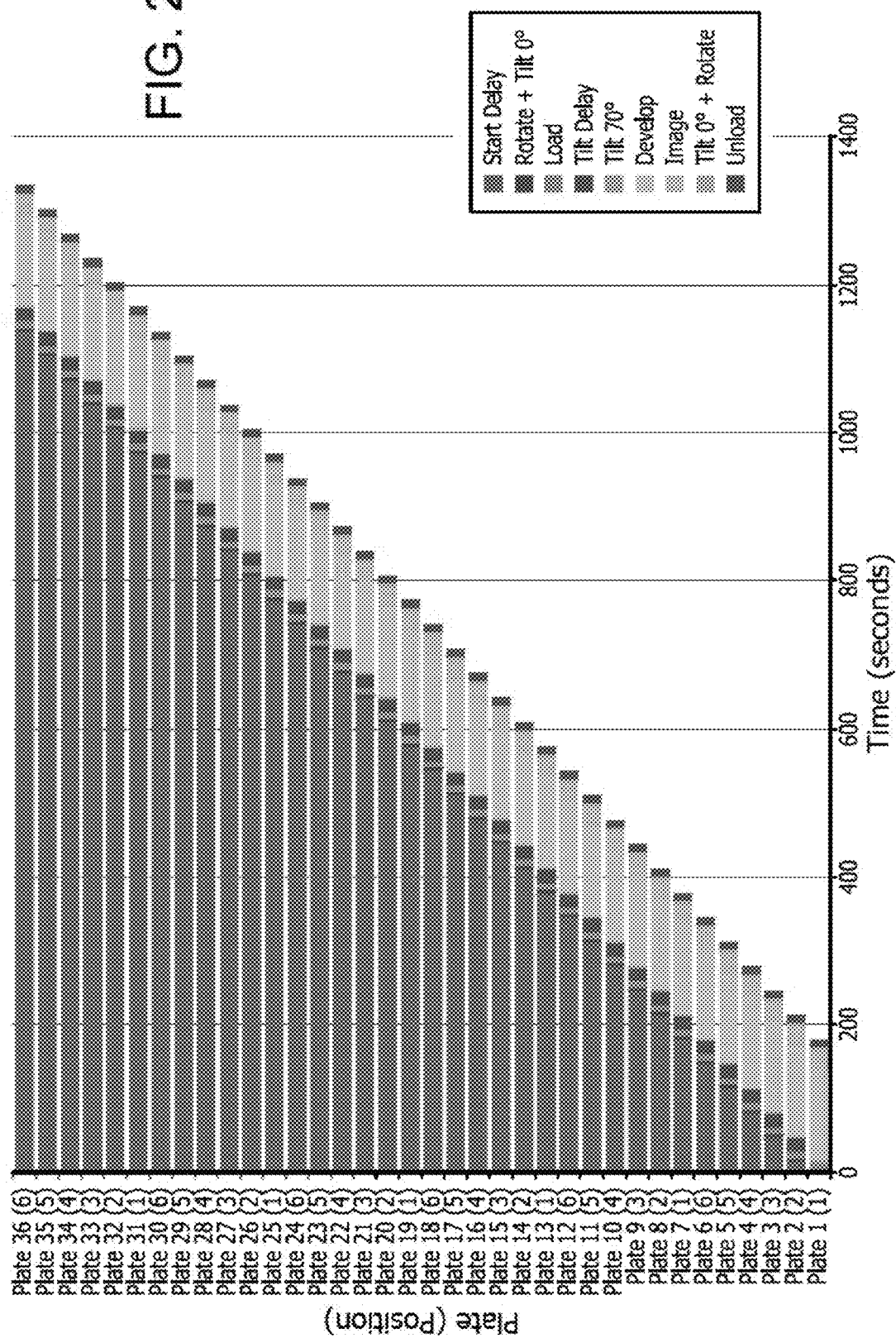
FIG. 25 is a timing diagram for automated imaging of 36 plates, in accordance with embodiments of the invention.

Typical timing diagrams are shown in FIGS. 24 and 25. The illustrated diagrams in FIGS. 24 and 25 take into account normal kinetic input parameters for 6 and 36 plates, respectively. The HIVE imager, discussed previously, processes approximately 100 plates in a single hour under normal operating conditions according to exemplary embodiments.

Figure 23:
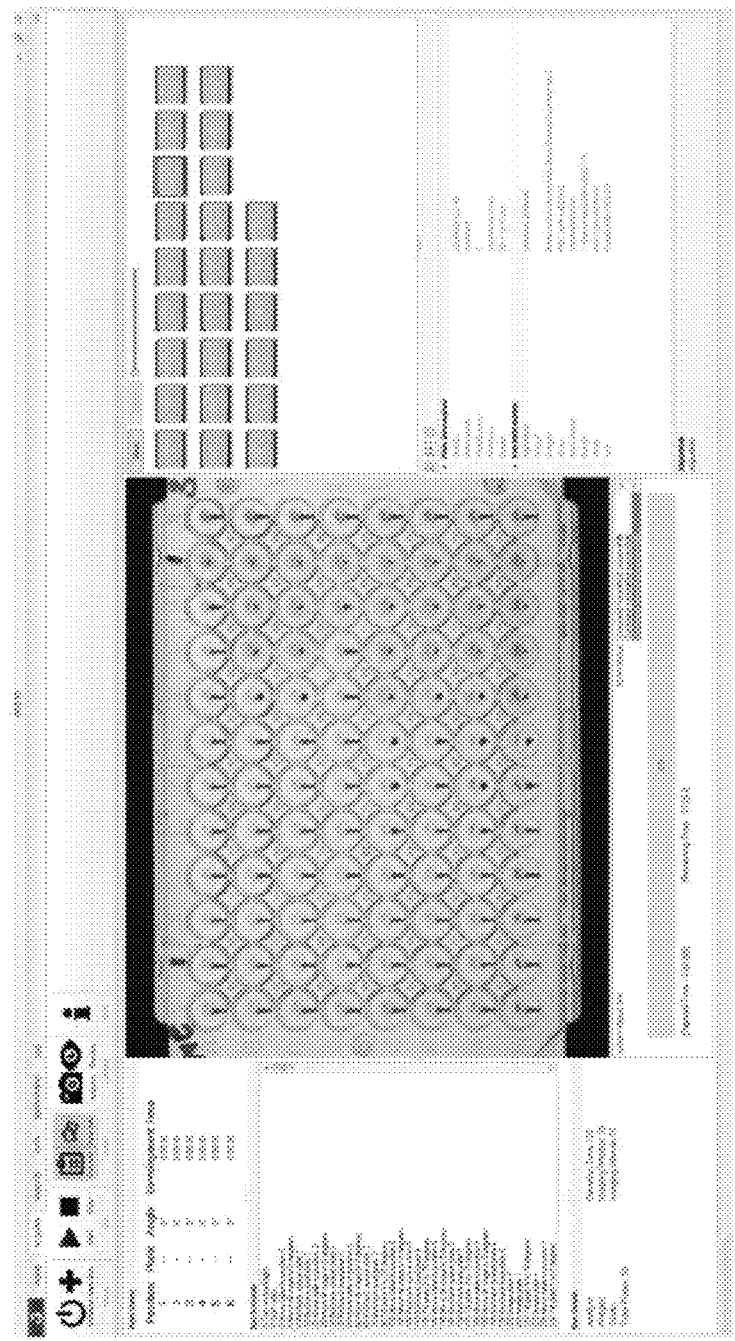
FIG. 23 illustrates an image acquisition tab for a GUI, in accordance with embodiments of the invention.

During a run, pertinent information is displayed by the image acquisition interface, such as, run completion percentage, current plate angle and development time, and kinetic imaging status. FIG. 23 illustrates an exemplary tab on the GUI which is displayed to the user during image acquisition. According to this embodiment video data of the current plate being imaged is displayed so that the user can observe the development process in real-time on a computer monitor. According to further embodiments thumbnail images are also displayed as plate images are acquired. Clicking on a thumbnail image, for example, loads the larger image in the video window of the GUI and also displays specific plate and run information.

FIGS. 24 and 25 illustrate exemplary timing diagramd with respect to automated imaging of 6 plates, and 36 plates, respectively, in accordance with embodiments of the invention.

Image Analysis

Figure 26:
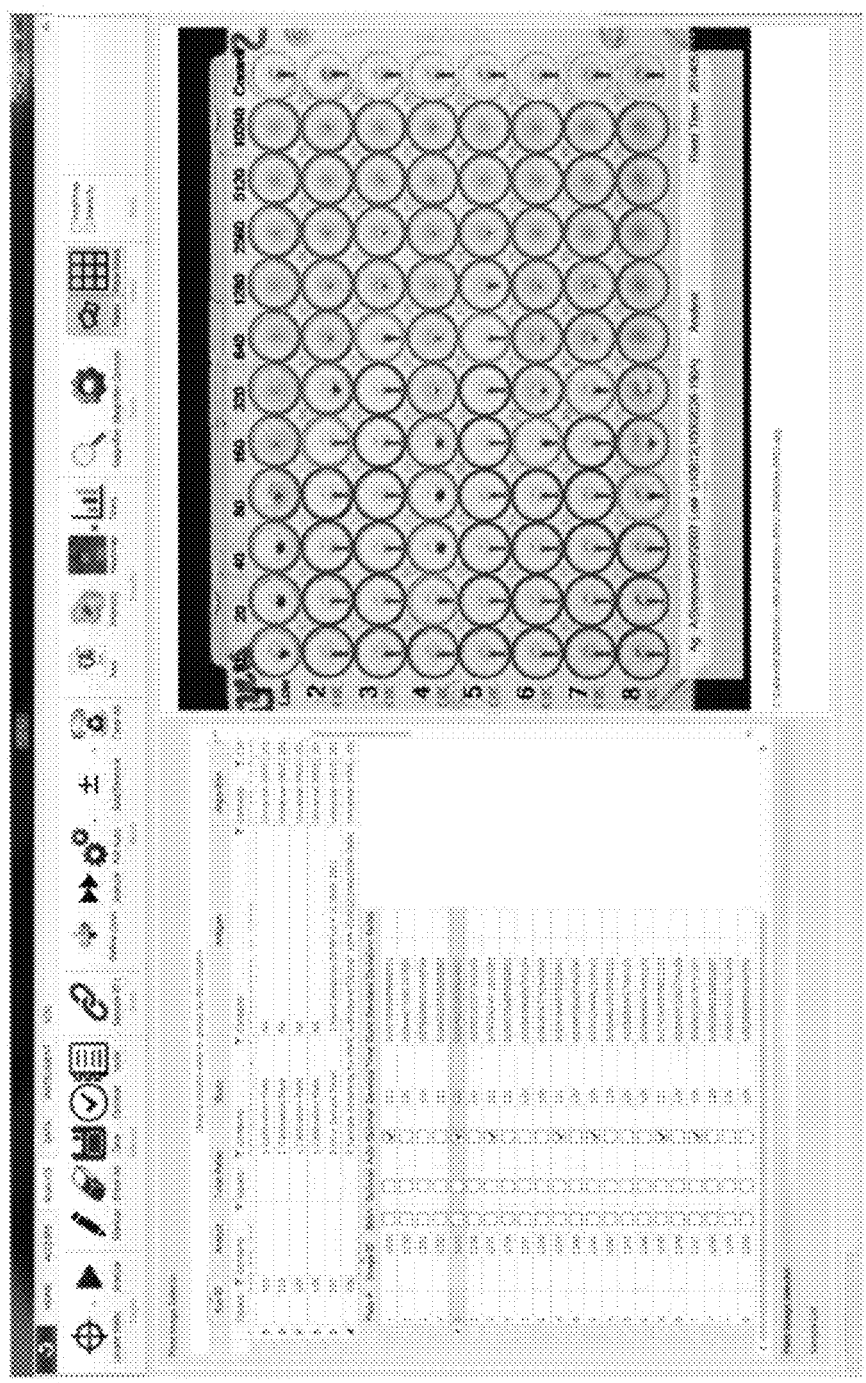
FIG. 26 is a further illustration of an image analysis tab for a GUI, in accordance with embodiments of the invention.

The image analysis component of the GUI according to this and other embodiments applies the image processing algorithm to an acquired whole-plate image and provides a visual representation of the result in the form of an overlaid plate mask. FIG. 26 shows an exemplary screen shot that would be displayed during image analysis in accordance with this embodiment. As shown, the plate mask indicates agglutination states, titer values, outliers, sample numbers, dilutions and also includes metadata such as antigen and image acquisition time. A manual mode allows users to also analyze plates manually and mark titer values and outliers and add notes to the plate mask. Analysis results can also be viewed as a heat map with numeric values or as an intensity map. The plate image database can also be mined using an interactive and filterable table which allows users to quickly access plate images of interest based on several metadata categories, such as, antigen, analyst, time stamp and/or experiment.

Consistent with various embodiments of the image analysis mentioned, plate images are analyzed using several different selectable analysis modes: manual analysis, automatic single-plate analysis, batch analysis and full-automatic analysis.

Manual analysis mode allows users to manually mark the titer points on well images by, for example, left-clicking on the particular well of interest. Outlier wells are designated by, for example, right-clicking on those wells. Designated, or marked, wells are distinguished by, for example, colored and/or dashed circles around their perimeter. Results are then saved to the database and can be retrieved in a later session as desired. Automatic single-plate analysis mode according to this and other embodiments provides for the analysis of a single selected plate and returns the titer values and agglutination states. According to batch analysis mode, all plate images contained within a defined batch are serially analyzed. Analysis progress is indicated to the user by a progress bar and status message indicating the plate being analyzed as well as remaining plates. Full automatic analysis mode processes plates using the optimal time point algorithm. When this mode is employed processing can be performed on images from a single plate or an entire run of plates.

According to further embodiments, several different view modes are implemented on the analysis tab (for example as shown in FIG. 26) for viewing the results of the analysis: plate mask, intensity map, heat map and charts.

The plate mask is a false color overlay that indicates the agglutination state of the wells, titer values, validity of the RBC controls and outliers due to discontinuous agglutination states. The plate mask also overlays the dilution factor for each column, sample number for each row and a notes section that contains, for example, analyst name, plate time stamp, antigen used and an area for custom notes. The intensity map is a false color image of the segmented RBC patterns from all wells, shaded as a function of pixel intensity. This is useful, for example, for reviewing how the algorithm is segmenting the patterns and provides insight to how the algorithm is assigning titer values. The heat map is an 8 by 12 grid representation of an HAI plate with the color of each section defined by the HA-Parameter value of the corresponding well. It is useful for visualizing the onset of agglutination for a sample as a color change is observed during the transition from non-agglutinated to agglutinated. Lastly, a charts section is included on the analysis tab according to this embodiment to display data for a selected plate, data such as, RBC control well standard deviation values, sample titer values and dose response curves.

Data Handling

Figure 27:
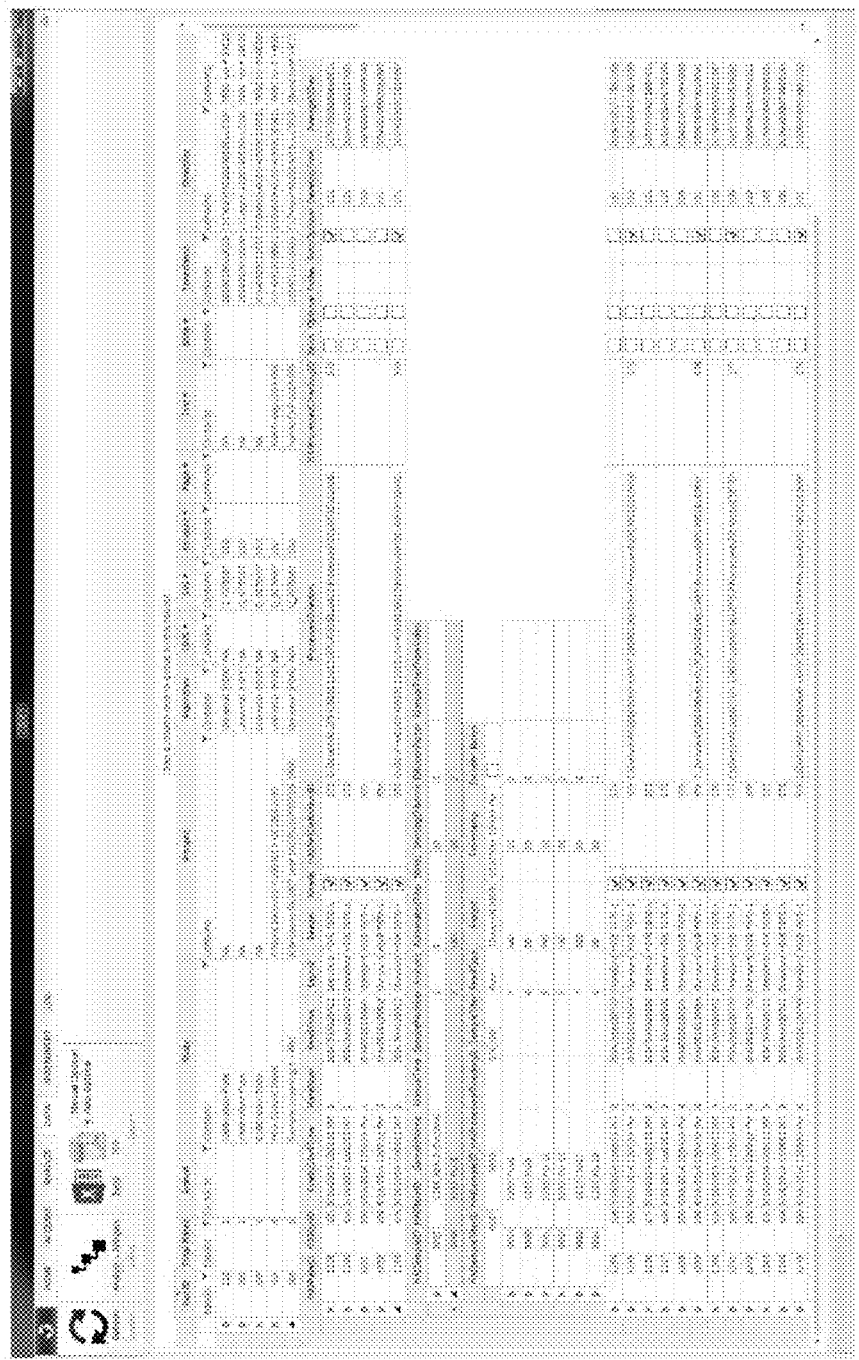
FIG. 27 illustrates a data analysis tab for a GUI, in accordance with embodiments of the invention.

According to embodiments of the invention, a data management GUI component provides controls for mining and exporting the data generated by the image analysis component. FIG. 27 is a screen-shot of an exemplary data analysis tab presented to the user consistent with this embodiment. For example, an interactive and filterable table, as shown, provides the ability to create and export data subsets based on metadata within the hierarchal structure of Run→Plate-→Sample→Titer. Export control provided in accordance with this and other embodiments generates pre-formatted, custom Microsoft Excel, or some other format, reports directly from the relational database. According to further embodiments data is exported in a custom formatted pdf report.

Configuration

Configuration of the data analysis settings, instrument settings and user roles is handled through a tab-based menu generated within the GUI. For example, according to one or more embodiments all parameters that are used in the image processing algorithms discussed previously are defined in the Analysis Settings menu. Hardware settings, such as, stage offsets, camera settings and communication ports, are controlled and defined via the Hardware tab of the settings menu. Additionally, according to at least one embodiment, the software supports three different user roles: general, manager and administrator. The permissions for each of these respective roles, as well as settings for specific users, are controlled and defined via the Users tab of the settings menu.

During testing, a significant amount of kinetic image data for several different influenza antigens has been acquired using the prototypes and the HIVE imager in accordance with the various embodiments disclosed herein. This data has been used to develop and refine the image processing algorithm disclosed and further define instrument design requirements for the hardware. Concordance testing was performed with the embodiments using the prototype 3 and HIVE imaging systems, each in two independent assay runs with different qualified analysts and different lots of turkey red blood cells. A total of 2 results per sample per antigen were generated with each reading method, manual and automated. Automated titer assignment was defined by the algorithm disclosed using the optimal static image defined by the optimal time point algorithm disclosed. Sample panels consisted of 60 human serum samples comprising 30 paired serum samples from pre and post vaccination with the 2012-2013 influenza vaccine. Antigens tested included H1N1, H3N2, B and ether-treated B. Statistical analysis of the results comprised a standard concordance analysis of individual assay runs and geometric mean titers (GMT) of both assay runs, Committee for Medicinal Products for Human Use (CHMP) criteria including percent seropositivity, percent seroconversion and GMT ratio (GMTR, post/ pre), and analysis of precision using individual reading methods. Concordance analysis between the current method of manual read of streaming RBCs and automated analysis using the imagers according to embodiments of the invention has shown excellent agreement for a wide range of influenza strains. The data provided in the tables of FIG. 28 and FIG. 29 demonstrates the high level of concordance between manual and automated analysis for various influenza strains when the embodiment using the prototype 3 imaging system was used. The data provided in the tables of FIG. 30 and FIG. 31 demonstrates an even higher level of concordance between manual and automated analysis when the embodiment using the HIVE imaging system was used. Agreement between manual and automated reading methods using the imagers according to embodiments of the invention has also been demonstrated for other strains including B/Hubei-Wujiagang/158/2009 (both whole and ether-treated) as well as B/Florida/04/2006 (data not shown). The various algorithms disclosed herein have also shown strain independence, as the algorithm parameters such as limits, thresholds, and color gating were fixed for all strains tested on the respective imagers.

Figure 32:
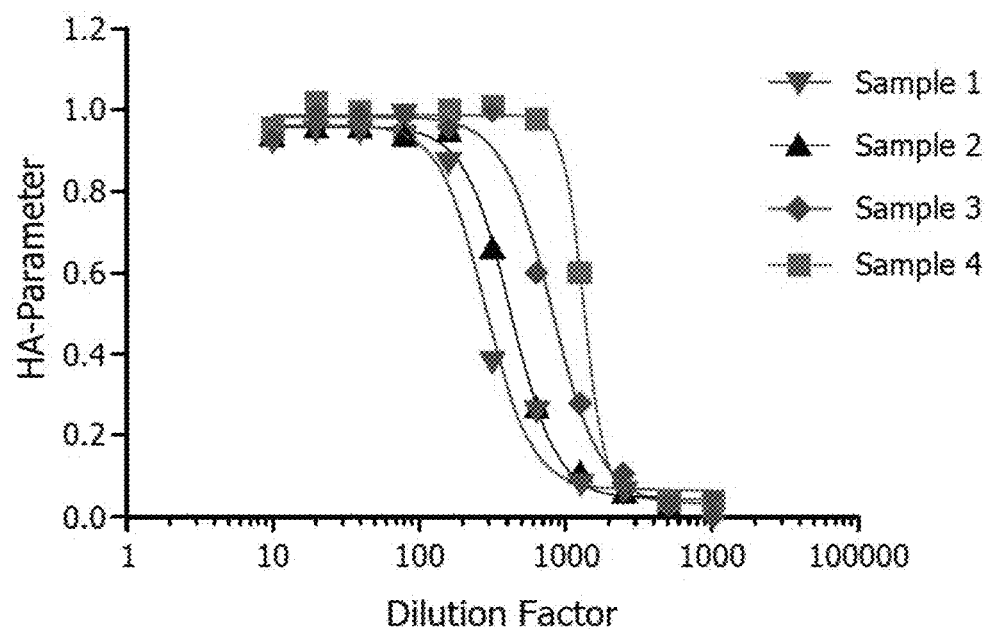
FIG. 32 is a chart showing curve fitting HAI data, in accordance with embodiments of the invention.

Image processing provides expanded capability for analyzing the HAI compared to traditional analysis by assigning a quantitative measure to the agglutination state. An HAI sample dilution series can be fit to a dose response curve using these numeric values (HA-Parameters). As shown, for example, in FIG. 32, the dose response curve makes it possible to assign continuous titer values, essentially interpolating the discrete values that are traditionally reported. The result is greater precision and more accurate depiction of the actual titer at which agglutination begins.

Figure 33:
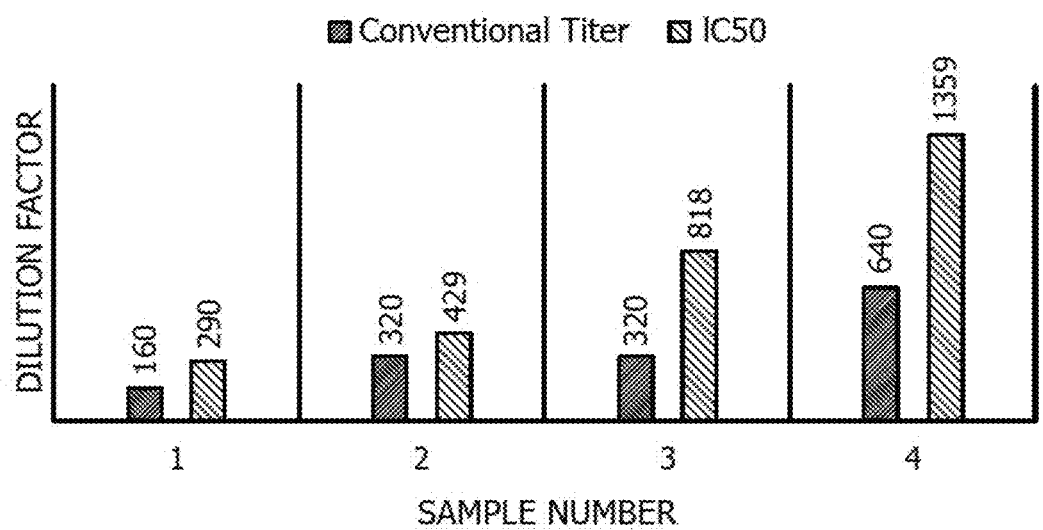
FIG. 33 is a chart comparing conventional titer values with $IC_{50}$ values, in accordance with embodiments of the invention.

The resulting curve is analogous to an inhibition response curve which is useful for determining the concentration of a substance, called the inhibitor or antagonist, required to inhibit agonist activity by a certain amount, normally reported as the half maximal inhibitory concentration or $IC_{50}$. In the case of HAI, the $IC_{50}$ value describes the sample dilution factor required to reduce the HA-Parameter by half. As the HA-Parameter is related to agglutination state, the $IC_{50}$ value then provides a means to classify a sample based on degree of agglutination rather than discrete classifications of agglutinated or non-agglutinated. The dose response curves in FIG. 32, for example, each represent the dilution series for a different serum sample. The corresponding $IC_{50}$ value for each curve is plotted in FIG. 33 along with the traditional discrete titer value for the sample. Of note are samples 2 and 3 which have the same conventional titer value of 320, but significantly different $IC_{50}$ values. The difference between the dose response curves for these samples is evidenced in FIG. 32 where the curve for sample 3 is shifted to the right compared to the curve for sample 2, suggesting they exhibit dissimilar agglutination activity. However, their conventional titer values are the same based on the criteria for assigning discrete values. In this case, the dose response curves and $IC_{50}$ values provide a more complete representation of the sample agglutination states.

What is claimed is:

1. A method for determining functional binding activity of an antibody, comprising:
   (a) preparing a sample consisting of an agglutinating factor and said antibody in at least one well of a plate comprising an array of test wells;
   (b) adding a target object to said sample of (a) under conditions permitting agglutination of said target object by said agglutinating factor;
   (c) preparing an image of said sample of (b) with said target object added using a system comprising:
   (i) an optical path, the optical path comprising:
      a camera,
      a lens, and
      a mirror;
   (ii) a rotating table comprising a plurality of plate holding stations and a table motor for rotating the rotating table to move any of the plate holding stations into alignment with the optical path, each plate holding station of the plurality of plate holding stations comprising:
      a plate holder for holding a plate comprising an array of test wells, and
      a tilt motor for adjusting a tilt angle of the plate holder; and
   (iii) a controller for controlling the table motor, the tilt motor, and the camera to acquire at least one image of at least one plate, wherein the plate comprising the sample in the at least one well is disposed in the plate holder; and
   (d) processing said image in a programmed processing device to determine agglutination of said target object and thereby determining functional binding activity of the antibody.

2. The method for determining functional binding activity of the antibody recited in claim 1, wherein said plate is a culture plate having an array of test wells.

3. The method for determining functional binding activity of the antibody recited in claim 1, wherein said image includes image data for each of the wells containing sample and target object.

4. The method for determining functional binding activity of the antibody recited in claim 1, wherein in step (c) said plate is tilted at an angle and said plate is illuminated with a light source prior to preparing the image.

5. The method for determining functional binding activity of the antibody recited in claim 4, wherein the angle is about 0 degrees or about 70 degrees.

6. The method for determining functional binding activity of the antibody recited in claim 4, wherein the angle is between about 0 degrees to about 70 degrees.

7. The method for determining functional binding activity of the antibody recited in claim 1, wherein a plurality of plates each having a respective plurality of wells are independently imaged and processed automatically.

8. The method for determining functional binding activity of the antibody recited in claim 2, wherein a plurality of plates each having a respective plurality of wells are independently imaged and processed automatically.

9. The method for determining functional binding activity of the antibody recited in claim 3, wherein a plurality of plates each having a respective plurality of wells are independently imaged and processed automatically.

10. The method for determining functional binding activity of the antibody recited in claim 4, wherein a plurality of plates each having a respective plurality of wells are independently imaged and processed automatically.

11. The method for determining functional binding activity of the antibody recited in claim 5, wherein a plurality of plates each having a respective plurality of wells are independently imaged and processed automatically.

12. The method for determining functional binding activity of the antibody recited in claim 7, wherein up to six plates are tilted simultaneously.

13. The method for determining functional binding activity of the antibody recited in claim 1, wherein the plates are imaged from the bottom-up.

14. The method for determining functional binding activity of the antibody recited in claim 1, wherein the optical path of the system comprises a telecentric lens.

15. The method for determining functional binding activity of the antibody recited in claim 10, wherein up to 100 plates per hour in a tilted configuration are independently imaged and processed automatically.

16. The method for determining functional binding activity of the antibody recited in claim 7, wherein where up to 300 plates per hour in a non-tilted configuration are independently imaged and processed automatically.

17. The method for determining functional binding activity of the antibody recited in claim 1, wherein the system used in the image preparation step (c) is integrated into an automation line and accessible by automated plate handlers.

18. The method for determining functional binding activity of the antibody recited in claim 17, wherein the automated plate handler is a robotic arm.

19. The method for determining functional binding activity of the antibody recited in claim 17, wherein the automated plate handler is a stacker.

20. The method for determining functional binding activity of the antibody recited in claim 17, wherein the automated plate handler is a crane.

* * * * *